(12) United States Patent
Acker et al.

(10) Patent No.: US 6,599,256 B1
(45) Date of Patent: Jul. 29, 2003

(54) OCCLUSION OF TUBULAR ANATOMICAL STRUCTURES BY ENERGY APPLICATION

(75) Inventors: David E. Acker, Setauket, NY (US); Louis R. Kavoussi, Lutherville, MD (US); Bharat B. Pant, Stony Brook, NY (US); Patrick David Lopath, East Setauket, NY (US); Emad S. Ebbini, Edina, MN (US)

(73) Assignee: Transurgical, Inc., Setauket, NY (US)

( * ) Notice: Subject to any disclaimer, the term of this patent is extended or adjusted under 35 U.S.C. 154(b) by 60 days.

(21) Appl. No.: 09/659,068

(22) Filed: Sep. 11, 2000

(51) Int. Cl.[7] ............... A61H 1/00; A61H 1/02; A61H 5/00
(52) U.S. Cl. ............... 601/2; 601/3; 604/22; 600/439
(58) Field of Search ............... 601/2, 3; 604/20, 604/22, 24; 600/439

(56) References Cited

U.S. PATENT DOCUMENTS

| | | | |
|---|---|---|---|
| 4,073,289 A | 2/1978 | Fahim ............... | 128/24 |
| 4,554,925 A | 11/1985 | Yound ............... | 128/653 |
| 4,620,546 A | 11/1986 | Aida et al. ............... | 128/660 |
| 4,920,982 A | 5/1990 | Goldstein ............... | 128/842 |
| 4,951,688 A | 8/1990 | Keren ............... | 128/804 |
| 4,983,177 A | 1/1991 | Wolf ............... | 606/157 |
| 5,065,751 A | 11/1991 | Wolf ............... | 128/831 |
| 5,247,935 A | 9/1993 | Cline et al. ............... | 128/653 |
| 5,469,867 A | 11/1995 | Schmitt ............... | 128/898 |
| 5,769,790 A | 6/1998 | Watkins et al. ............... | 600/439 |
| 5,792,138 A | 8/1998 | Shipp ............... | 606/38 |
| 5,826,584 A | 10/1998 | Schmitt ............... | 128/898 |
| 5,891,141 A | 4/1999 | Rydell ............... | 606/45 |
| 6,088,613 A | 7/2000 | Unger ............... | 600/420 |

FOREIGN PATENT DOCUMENTS

WO    WO 98/52465    11/1998

*Primary Examiner*—Marvin M. Lateef
*Assistant Examiner*—Jeoyuh Lin
(74) *Attorney, Agent, or Firm*—Lerner, David, Littenberg, Krumholz & Mentlik, LLP

(57) ABSTRACT

A tubular anatomical structure in a mammalian subject is occluded by directing ultrasonic energy from outside of the body. For example, a male subject may be sterilized by directing ultrasonic energy through the skin of the scrotum, onto the vas deferens. The focal spot of an ultrasonic transducer may be registered with the structure to be treated by means of guide members on a probe holding the transducer. The procedure is simple and can be entirely non-invasive. Apparatus for performing this and other treatments may be provided as a disposable unit, and the guide members may be arranged to hold a fold of tissue without substantially obstructing the sonic path from the transducer to the fold.

46 Claims, 11 Drawing Sheets

US 6,599,256 B1

OCCLUSION OF TUBULAR ANATOMICAL STRUCTURES BY ENERGY APPLICATION

CROSS-REFERENCE TO RELATED APPLICATIONS

The present application claims benefit of U.S. Provisional Patent Application No. 60/153,432, filed Sep. 10, 1999, the disclosure of which is hereby incorporated by reference herein.

BACKGROUND OF THE INVENTION

In numerous medical and veterinary procedures, it is desirable to occlude a tubular anatomical structure such as a blood vessel or a tubular structure in the respiratory, digestive, reproductive or urinary tract of a mammalian subject. These procedures have been performed by surgical intervention as, for example, by making an artificial opening in the body to expose the tubular structure and ligating the tubular structure, by tying a suture around the structure and pulling the suture tight so as to clamp the structure shut. Alternatively, the structure may be cut apart and the open ends may be left in place. The open ends do not reunite with one another, and therefore the structure is occluded. In other procedures, tubular structures have been cauterized by application of heat or other forms of energy within the body. For example, U.S. Pat. No. 5,891,141 discloses an instrument with a set of electrodes which can be inserted through a surgically-created opening in the body to grasp a tubular structure between the electrodes so that radio frequency ("RF") electrical energy can be applied directly to the tissue forming the wall of the structure. Coagulation of the tissue occludes the structure, whereupon the structure is severed by a cutting blade carried on the instrument. Surgical invasion of the body poses at least some risks even if minimally-invasive surgical procedures are employed. Other techniques for occluding anatomical structures include insertion of artificial plugs into such structures as, for example, by threading a catheter or other invasive device into the structure and dispensing a mass of biologically compatible plug material from the tip of the catheter. These techniques require careful selection of the plug material and careful attention to dispensing technique and also require insertion of an instrument into the body.

One example of a procedure which involves occlusion of a tubular anatomical structure is vasectomy, a common male sterilization procedure. A vasectomy is a procedure which occludes or severs the vas deferens so that it cannot serve as a passage for sperm from the testes to the urinary tract. Vasectomies have been performed by surgically opening the scrotum and cutting the vas deferens. Although this is a minor surgical procedure, there is nonetheless some risk associated with it. Also, if the subject later desires to reverse the vasectomy, it is difficult to locate the severed ends to reconnect them with one another. Typically, the ends of the vas deferens retract away from one another with time.

Techniques have been developed for applying hyperthermia to tissue within a living subject by directing energy into the subject from outside the subject's body. For example, in high intensity focused ultrasound ("HIFU") techniques, ultrasonic energy is applied from a source disposed outside the subject's body and directed into the subject body in such a manner that the ultrasonic energy comes to a focus at a selected focal point within the body. The focused ultrasonic energy heats the tissue at the focal point. Such techniques have been applied, for example, to ablate unwanted tissues such as tumors, or to potentiate the action of a drug at a particular location within the body. As used in this disclosure, the term "outside the subject's body" refers to a location which is either outside of the skin or within the alimentary tract, respiratory tract, or another structure of the body which is naturally open to the outside environment. Thus, a location inside of the mouth or rectum would be considered outside of the body. Because the ultrasonic energy can be applied from outside the body, the ultrasonic hyperthermia procedure can be essentially non-invasive. Techniques of this general type are described in PCT International Publication WO 98/52465, the disclosure of which is incorporated by reference herein. Other techniques for performing hyperthermia utilize radio frequency ("RF") energy instead of ultrasonic energy.

SUMMARY OF THE INVENTION

One aspect of the present invention provides methods of occluding a tubular anatomical structure in the body of a mammalian subject. Methods according to this aspect of the invention desirably include the step of directing ultrasonic energy from outside of the subject's body, into the body and onto the tissue constituting the tubular anatomical structure to thereby kill at least some of such tissue at a location along the length of the anatomical structure, whereby scar tissue will form and occlude the anatomical structure. Desirably, this is accomplished without substantially destroying tissue other than the tissue defining the wall of the tubular anatomical structure. Most preferably, the step of directing ultrasonic energy into the body is performed using a probe having one or more ultrasonic transducers associated therewith and adapted to emit ultrasonic energy so that the ultrasonic energy will be focused in a focal region at known disposition relative to the probe. The probe is positioned and maintained at a preselected disposition relative to a portion of the subject's body incorporating the tubular anatomical structure so that the focal region encompasses the anatomical structure.

In certain methods according to this aspect of the invention, the probe is positioned relative to the body of the subject without using an image of the internal structures within the body. For example, the step of maintaining the probe in a preselected disposition relative to the portion of the subject's body containing the tubular anatomical structure may be performed by engaging one or more guide members connected to said probe with such portion of the subject's body. The guide members desirably include a pair of opposed guide members projecting from the probe so that a portion of the subject's body, such as a fold of skin containing the tubular anatomical structure is pinched between the opposed guide members. Thus, the tubular anatomical structure is held in registration with the transducer and with the focus of the ultrasonic energy by the guide members.

A further aspect of the invention provides techniques for sterilizing a male mammalian subject, such as a human or non-human mammal. The spermatic ducts of such a subject, including the vas deferens, lie close to the skin of the scrotum. Thus, a portion of the scrotum such as a fold of scrotal tissue containing the vas deferens or other spermatic duct can be engaged with guide members of a probe as discussed above and ultrasonic energy can be directed through the skin of the scrotum covering this fold, onto the spermatic duct, to heat the tissue constituting the wall of the spermatic duct and preferably to kill at least some of this tissue. Scar tissue formed as a result of this procedure effectively occludes the spermatic duct, rendering the subject sterile. The procedure can be performed rapidly, typically in a few minutes or less, and can be performed entirely non-invasively. Further, because the ends of the spermatic duct are not separated from one another, they can be more readily reunited with one another at a later date.

A further aspect of the invention provides apparatus for occluding a tubular anatomical structure. Apparatus according to this aspect of the invention preferably includes a probe including a housing having an operative region and one or more ultrasonic transducers operatively associated with said housing. The transducer or transducers are adapted to deliver ultrasonic energy at a focal region having a known disposition relative to the operative region of the housing. Apparatus according to this aspect of the invention preferably also includes one or more guide members projecting from the housing for engaging a portion of a subject's body containing the anatomical structure to be occluded so as to hold that portion of the body in position relative to the operative region of the housing so that the focal region will lie at a known disposition relative to the body portion engaged by the guide members. This disposition most desirably is selected so that the focal region encompasses the tubular anatomical structure at one or more points along the length of such structure.

Preferably, the one or more guide members are adapted to engage the skin of the subject's body covering the engaged portion of the body. The guide members most preferably include first and second opposed guide members adapted to receive a portion of the body between them and to maintain that portion of the subject's body in preselected disposition relative to the housing of the probe and hence in a preselected disposition relative to the transducer. Most preferably, one or both of the guide members is movable relative to the housing so that said guide members can be moved toward and away from one another so as to pinch a portion of the subject's body, such as a fold of tissue encompassing the tubular anatomical structure, in a gap between the guide members.

In a particularly preferred arrangement, the guide members are adapted to pinch the portion of the body in a gap between the guide members so that the pinched portion projects generally in a first direction, referred to in this disclosure as the Z direction, relative to the guide members and the probe. The one or more transducers most preferably defines an emitting surface offset in the Z direction from the gap between the guide members, so that the emitting surface will be spaced from the body portion pinched between the guide members. However, the transducer or transducers desirably are arranged relative to the guide members so that the ultrasonic energy will have a focal region or region of maximum intensity extending in the gap between the guide members. The apparatus desirably also includes a flexible sonic transmission element such as a fluid-filled bag extending between the emitting surface and the gap between the guide members so that the flexible sonic transmission element will engage the skin of the pinched portion of the body held in the gap.

In a particularly preferred arrangement, the emitting surface is substantially in the form of a sector of a cylindrical surface having an axis extending in an axial or Y direction transverse to the Z direction. The guide members desirably are movable towards and away from one another generally in an X direction transverse to the axial or Y direction and also transverse to the Z direction. The transducer defines a central or medial plane including the axis of the cylindrical sector and extending through the middle of the sector. The medial plane of the transducer desirably extends substantially in the Y and Z directions, so that the medial plane is transverse to the directions of movement of the guide members, and extends in the gap between the guide members. When a fold of tissue is pinched between the guide members, the medial plane of the transducer is substantially aligned with the medial plane of the fold. As further discussed below, the cylindrical-sector transducer will provide a generally slab-like focal region oriented along the medial plane. The focal region is effectively aligned within the fold of tissue so as to maximize heating within the fold and minimize heating at the skin surface.

In a particularly preferred arrangement, at least one of the guide members includes first and second elements spaced apart from one another, and defining a space therebetween. Desirably, each one of the guide members includes such spaced-apart elements. The fluid bag or other said sonic transmission element most preferably extends into these spaces, so that the transmission element wraps around the fold of tissue. This arrangement provides sonic paths from the transducer into the sides of the fold.

A further aspect of the invention provides methods of performing hyperthermia within the body of a mammalian subject. The method according to this aspect of the invention desirably includes the step of providing an exogenous ultrasonic contrast medium within the body of the subject, i.e., a medium introduced from outside the subject's body. The contrast medium has sonic propagation properties different than the sonic propagation properties of the tissue surrounding the medium. Most preferably, the contrast medium is a sonically dispersive medium including a fluid and a plurality of micro particles, such as gas-filled micro spheres, having acoustic impedance different from the acoustic impedance of the fluid. The method according to this aspect of the invention most preferably further includes the step of directing ultrasonic energy into the body and focusing the ultrasonic energy in a focal region encompassing at least a portion of the ultrasonic contrast medium. The ultrasonic energy is dissipated and converted to heat preferentially in the medium or at an interface between the medium and the tissue surrounding the medium so as to heat the tissue surrounding the medium. In methods according to this aspect of the invention, the heating effect desirably is substantial, so as to heat the tissue immediately surrounding the medium by at least about 5° C., and most desirably so as to heat the tissue by at least about 10° C. For example, the ultrasonic energy may heat the tissue surrounding the medium to a degree sufficient to kill at least some of such tissue as, for example, by heating the tissue to a temperature above about 45° C., and more preferably above about 60° C. The ultrasonic contrast medium may be disposed within a tubular anatomical structure, and the said ultrasonic energy may heat the tissue constituting the wall of the tubular structure at one or more locations along such structure, so that scar tissue will form in the tubular structure and occlude such structure.

These and other features and advantages of the present invention will be more readily apparent from the detailed description of the preferred embodiments set forth below, taken in conjunction with the accompanying drawings.

DETAILED DESCRIPTION OF THE PREFERRED EMBODIMENTS

Figure 1:
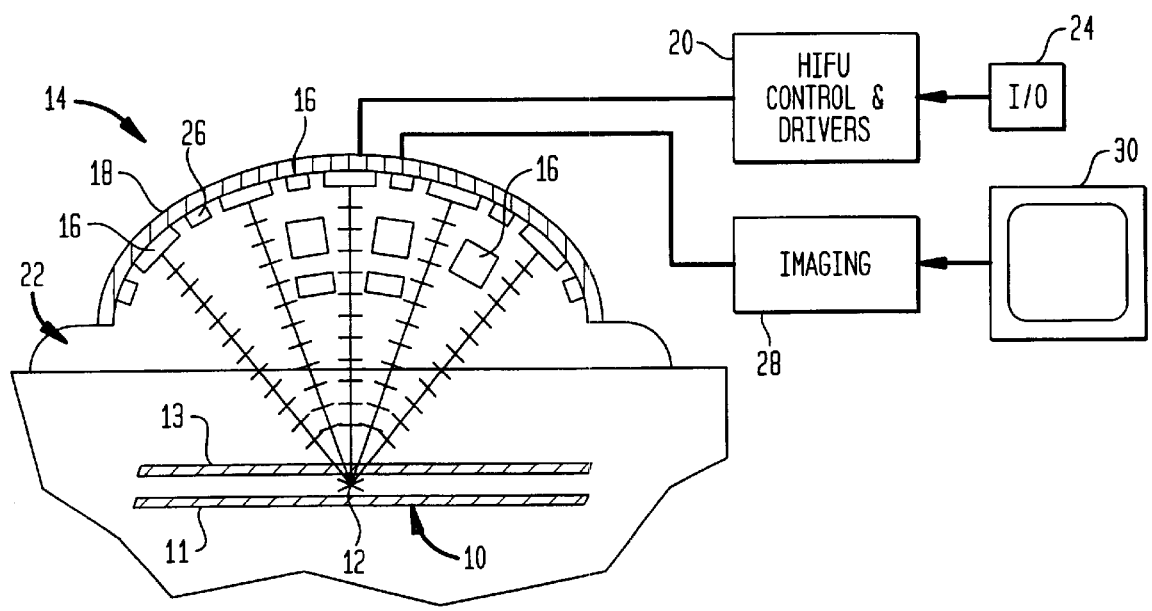
FIG. 1 is a diagrammatic view depicting apparatus used in a process in accordance with one embodiment of the invention.

In a method according to one embodiment of the present invention, a tubular anatomical structure disposed within the tissues of the body, such as the tubular structure 10 having a lining 11 surrounding an opening 13 is occluded by directing energy into the subject's body tissues from outside of the tissues, and outside of the subject's body, and onto a location 12 on the tubular structure. For example, the energy may be applied by a HIFU array 14 of the type disclosed in the aforementioned International Publication. As more fully described therein, such an array includes one or more transducers 16 mounted on a support 18. The array illustrated is an array as described in certain embodiments of such International Publication, in which the transducers are arranged along a dome-shaped sector of a sphere, as seen in cross-section in FIG. 1. The transducers are connected to a control and driving unit 20 which is adapted to excite the individual transducers so that they produce ultrasonic waves in the appropriate phase relationship for the waves to reinforce one another at focal location coincident with location 12. Such a transducer array typically is used in conjunction with a bag 22 filled with water or other energy-transmissive medium to assure efficient transmission of energy from the emitting transducers 16 to the tissues. As also more fully disclosed in the aforementioned International Publication, a HIFU array may be controlled so to steer the beam of ultrasonic energy by changing the phase relationships between the transducers and thus vary the aim point of the array. Also, the aim point can be moved by physically turning the array or individual transducers. Input/output devices 24 typically are linked to the control device for adjusting the aim point of the transducer array.

Where the anatomical structure to be occluded is disposed near the surface in a predictable location and is not surrounded by other sensitive structures, the correlation between the aim point of the ultrasonic energy and the anatomical structure can be established manually as, for example, by physically palpating the structure and marking its location on the skin and then placing the transducer array in the appropriate relationship to the mark on the skin. Where the tubular structure is disposed deep within the body, however, it is desirable to aim the ultrasonic energy using an image of the internal body structure. As described in the aforementioned International Publication, such an image may be acquired by magnetic resonance imaging and may also include previously-acquired imaging data transposed into a working frame of reference having a known relationship to the frame of reference of the ultrasonic array. Alternatively or additionally, the aim point may be selected using an ultrasonic imaging technique. The same transducer array used in application of a high intensity focused ultrasound may be used as an imaging transducer array in imaging the tissue. Alternatively or additionally, further transducers 26 may be provided in conjunction with the energy application transducers 16. These further transducers may be used to conduct a conventional ultrasonic imaging procedure so as to acquire image data. The image data is processed by a conventional ultrasonic image reconstruction apparatus 28 and displayed on a visual display 30 in the normal manner. The aim point of the ultrasonic array can be registered with the structure using such an ultrasonic image.

While the aim point of the ultrasonic energy applicator is set at the desired location 12 on anatomical structure 10, the HIFU controller and driver unit 20 actuates transducer array 16 to deliver ultrasonic energy so as to heat the tissue at location 12 and kill some or all of the tissue in the lining 11 surrounding the opening 13 of the tubular anatomical structure. This causes development of scar tissue which blocks the opening 13 of the anatomical structure. To enhance the blocking action, the tissue surrounding the anatomical structure may be maintained under compression, as by applying pressure through the skin or through the lining of the gastrointestinal tract during and after the heating step, so that the walls of the anatomical structure collapse upon one another at location 12.

This process provides several significant advantages. Because the tubular structure 10 is not cut, the structure remains intact at the location 12 where the procedure is performed. Therefore, there are no cut ends to be lost in surrounding tissue during the healing process. The procedure typically can be reversed by dissecting out the that portion of the structure containing the scar tissue blockage at location 12 and then immediately reconnecting the tubular structure at the dissected location. Also, the occlusion procedure may be substantially or entirely non-invasive.

Figure 2:
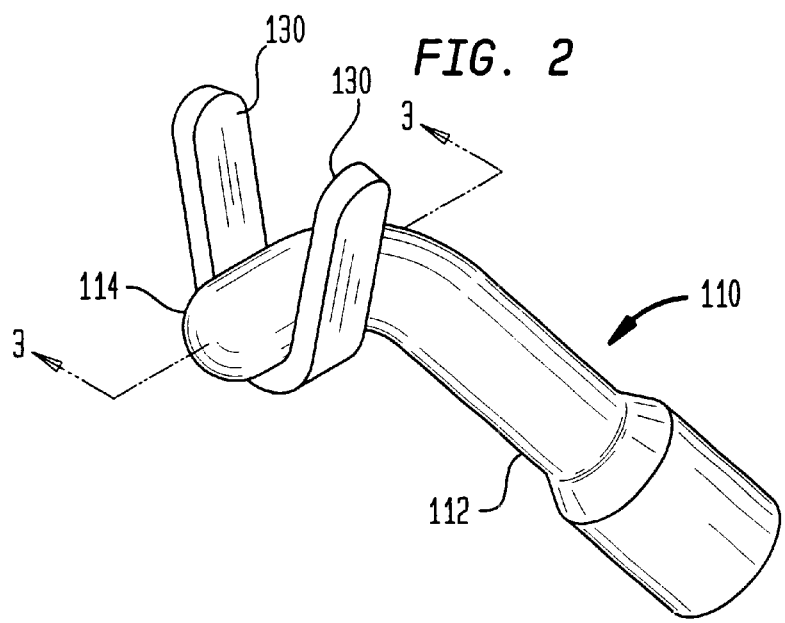
FIG. 2 is a diagrammatic perspective view depicting apparatus according to a further embodiment of the invention.
Figure 3:
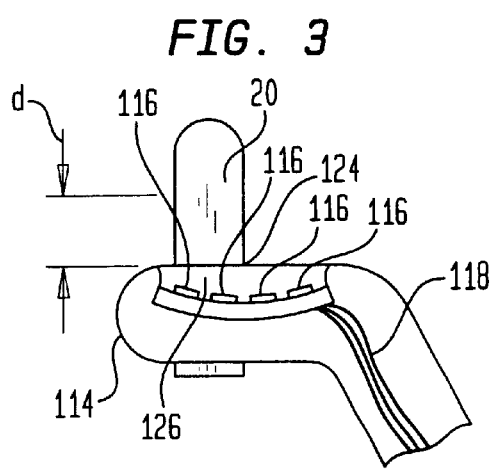
FIG. 3 is a fragmentary, diagrammatic sectional view taken along line 3—3 in FIG. 2.
Figure 4:
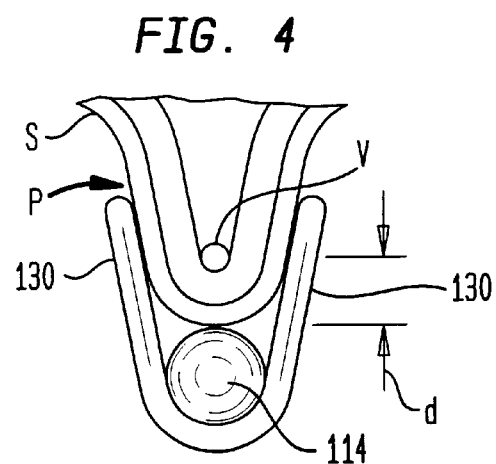
FIG. 4 is a fragmentary, diagrammatic view of the apparatus depicted in FIGS. 2 and 3 in conjunction with a portion of a subject.

The principles set forth above can be applied to vasectomy. As shown in FIG. 2, apparatus for performing vasectomies accords to one embodiment of the invention includes a probe 110 having a housing 112 defining a tip 114. An array of transducers 116 is disposed within the housing adjacent the tip. These transducers are connected to electrical cables 118 (FIG. 3) within housing 112 to power sources and drivers (not shown). The transducers are arranged in an array having a focal spot at a predetermined location 120 which lies at a depth d from the body surface. Depth d is selected so that it is approximately equal to the depth of the vas deferens beneath the surface of the scrotal skin. As further discussed below, the array of transducers can be replaced by a single curved transducer having a similar focus. The tip of the probe may include, or may covered with, a membrane 124 enclosing a transmission medium such as water 126 to couple the ultrasonic emissions from transducers 116 into the subject's tissues in use. As best seen in FIG. 2, a pair of guide members 130 project from the tip 114 of body 112 on opposite sides of the transducer array 116. These guide members form a generally V-shaped opening between them.

In a vasectomy procedure according to one embodiment of the invention, the physician manually locates the vas deferens by palpation and forms a pinched region P of the scrotal tissue S encompassing a portion of the vas deferens. The physician engages the pinched region of the scrotum between the guide members 130 so that the pinched region is positioned on the tip 114 of the housing 112. In this position, the vas deferens V is disposed at depth or spacing d from the surface of the tip 114. The physician now actuates the transducer array to apply a pre-selected dose of ultrasonic energy. The ultrasonic energy is automatically focused at the spot on the vas deferens, inasmuch as the ultrasonic energy is focused at depth d by the geometry of the system. Stated another way, the transducer array or single transducer is aimed without using an image of the internal structures within the subject's body, such as an ultrasound, X-ray or MRI image. The ultrasonic energy kills tissue lining the vas deferens at a location along the vas deferens and provokes scar tissue formation.

The procedure affords several significant advantages over conventional surgical vasectomy. It is non-invasive. Moreover, the vas deferens remains intact.

To reverse the procedure, the vas deferens can be surgically isolated from the surrounding tissue. The region affected by the ultrasonic ablation can be dissected out and the resulting ends can be reunited with one another. Because the vas deferens is not cut in the original procedure, the problem of losing the ends does not arise.

Figure 5:
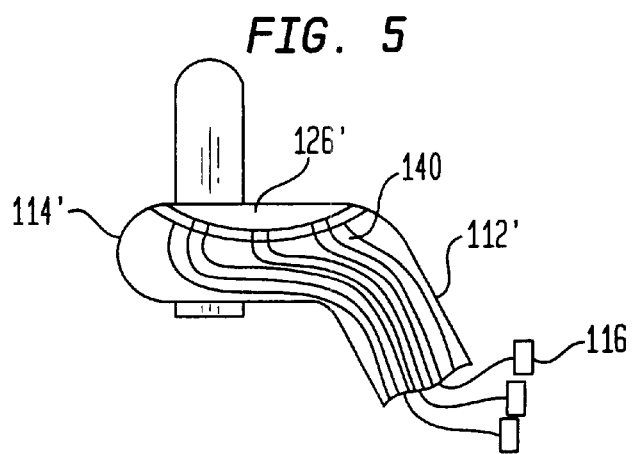
FIG. 5 is a view similar to FIG. 3 but depicting apparatus according to a further embodiment of the invention.

Numerous variations of the features discussed above can be utilized. For example, as shown in FIG. 5, the apparatus may incorporate waveguides 140 terminating adjacent the tip 114' of the instrument housing 112'. These waveguides may be connected to individual transducers 116' located in the housing remote from the tip or located outside of the housing unit in a separate unit. Ultrasonic energy supplied by the transducers 116 propagates through the waveguides and is emitted from the waveguides into the transmission medium 126'. For example, the wave-guides may be individual tubes filled with water or other liquid transmission medium continuous with the transmission medium 126' held at the tip. In this case, the ultrasonic energy does not pass through an interface as it passes from the waveguides into transmission medium 126'.

Figure 6:
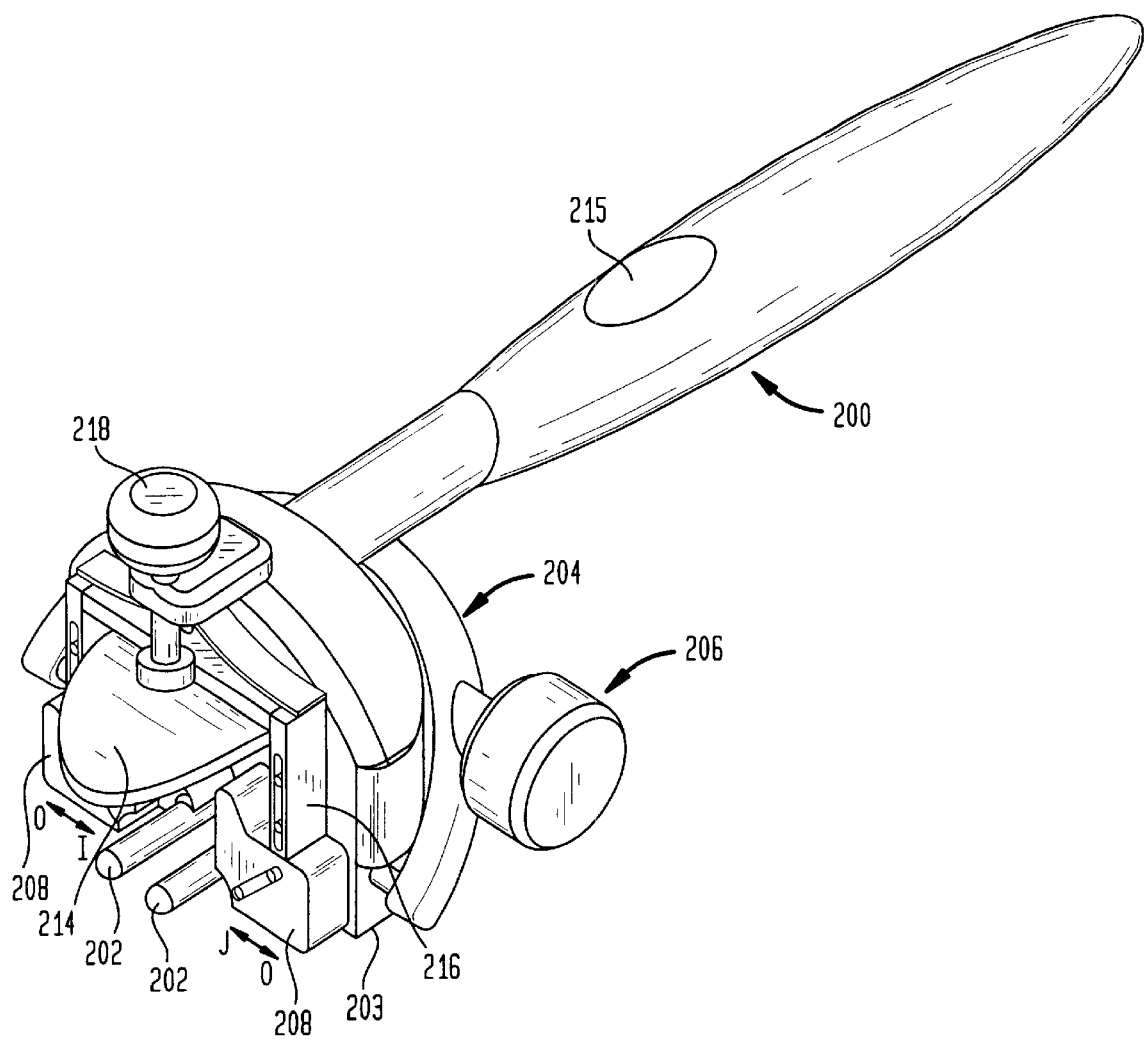
FIG. 6 is a perspective view depicting apparatus according to yet another embodiment of the invention.

A vasectomy apparatus according to a further embodiment of the invention (FIGS. 6 and 7) includes a body 200. A pair of clamping members 202 in the form of elongated cylindrical rods are mounted to carriers 203 which are slidably mounted to housing 200 for movement towards and away from one another. Clamping members 202 extend generally parallel to one another. A screw-type clamping mechanism 204 is linked to carriers 203 so that the carriers and clamping members 202 can be moved towards and away from one another in the inward direction I and outward direction O transverse to the axes of members 202 by adjusting the knob 206 of the clamping mechanism. A pair of guide members 208 are mounted by pins 210 and slots 212 to the housing 200 or to carriers 203 for movement along sloping paths, oblique to the inward and outward directions.

The device further includes a HIFU element 214 incorporating a single dish-shaped transducer. For example, the HIFU unit may include a rigid, dish-shaped backing and ceramic or polymeric piezoelectric material disposed on the interior of the backing. HIFU element 214 has a fixed focal location 213 at a predetermined distance from the element. The HIFU element is connected to a driver (not shown) controlled by a trigger 215 (FIG. 6) mounted on the body. The HIFU element is mounted to a carriage 216 for movement in a carriage-in direction CI and carriage-out direction CO perpendicular to the inward and outward directions I and O of the clamp movement. Movement of carriage 216 is controlled by a screw adjustment mechanism 218. The lower end of carriage 216 bears on guide members 208 so that as the carriage moves in the carriage-in direction CI (downwardly in FIG. 7) the guide members move downwardly and inwardly towards one another.

Figure 7:
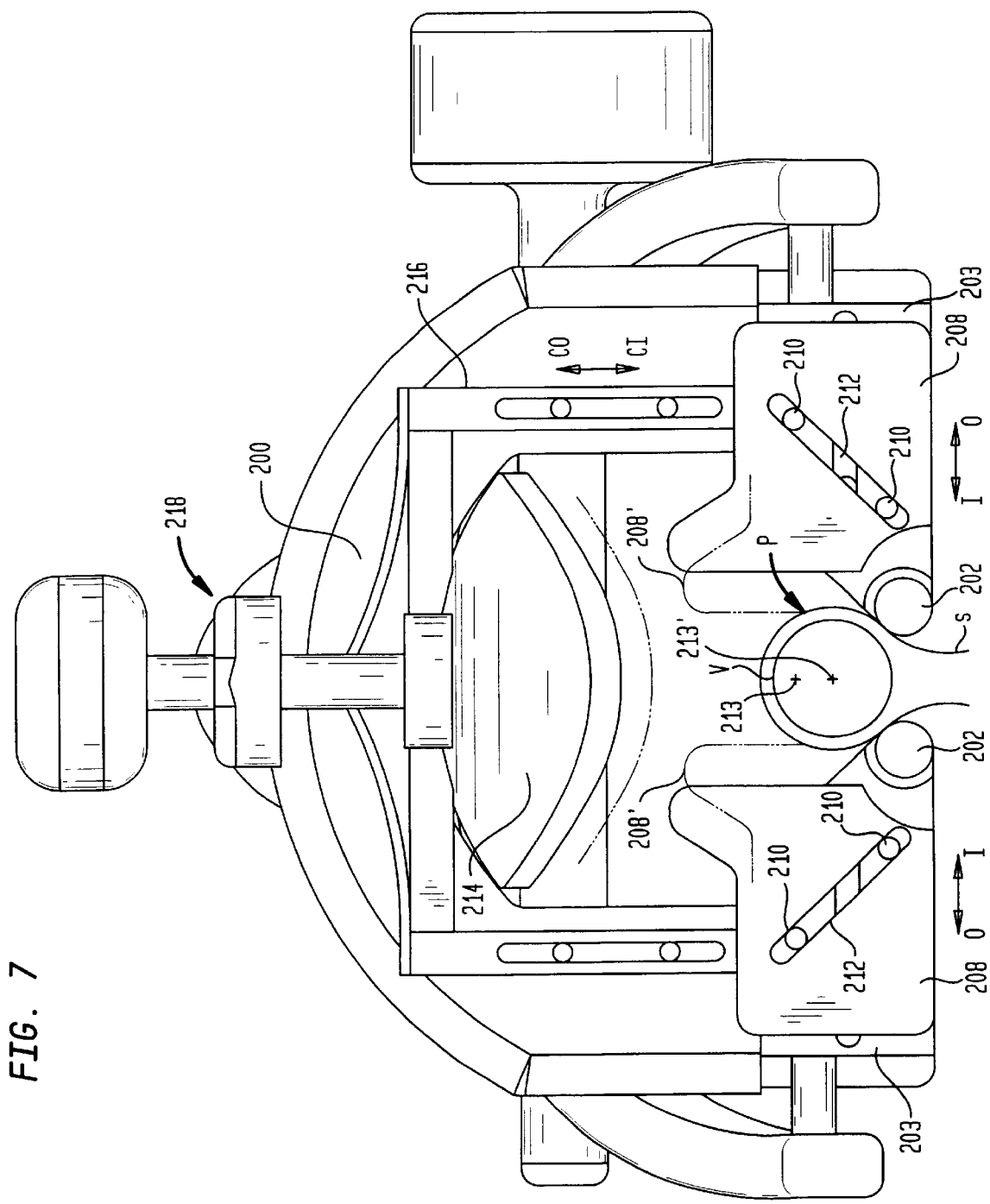
FIG. 7 is an elevational view of the apparatus shown in FIG. 6.

In operation, the physician positions a portion of the scrotum S between clamp elements 202, and adjusts the clamp elements to the position depicted in FIG. 7, thereby capturing a pinched region P of the scrotum, including the vas deferens V. The physician then adjusts carriage 216 in the carriage-in direction, until guide members 208 engage the pinched region of the scrotum as indicated in broken lines at 208' in FIG. 7. The geometry of carriage 216, HIFU element 214 and guide members 208 is selected so that when the guide members engage the surface of the scrotum in pinched region P, the focal spot of the HIFU element is positioned in the center of the vas deferens as-indicated at 213' in FIG. 7. The system automatically compensates for anatomical differences such as larger or smaller diameter of the vas deferens or thicker or thinner skin layers overlying the vas deferens. For example, with a thicker skin layer, the center of the vas deferens will be disposed slightly higher with respect to clamp elements 202. The thicker skin layer, however, will also arrest the guide members 208 at a wider spacing, and with carriage 216 at a higher elevation relative to the body 200 and clamp members 202, so that the focal spot is still positioned at the center of the vas deferens. The apparatus typically is used in conjunction with a balloon (not shown) filled with water or other sound-transmissive medium placed between the HIFU element and the scrotum.

Figure 8:
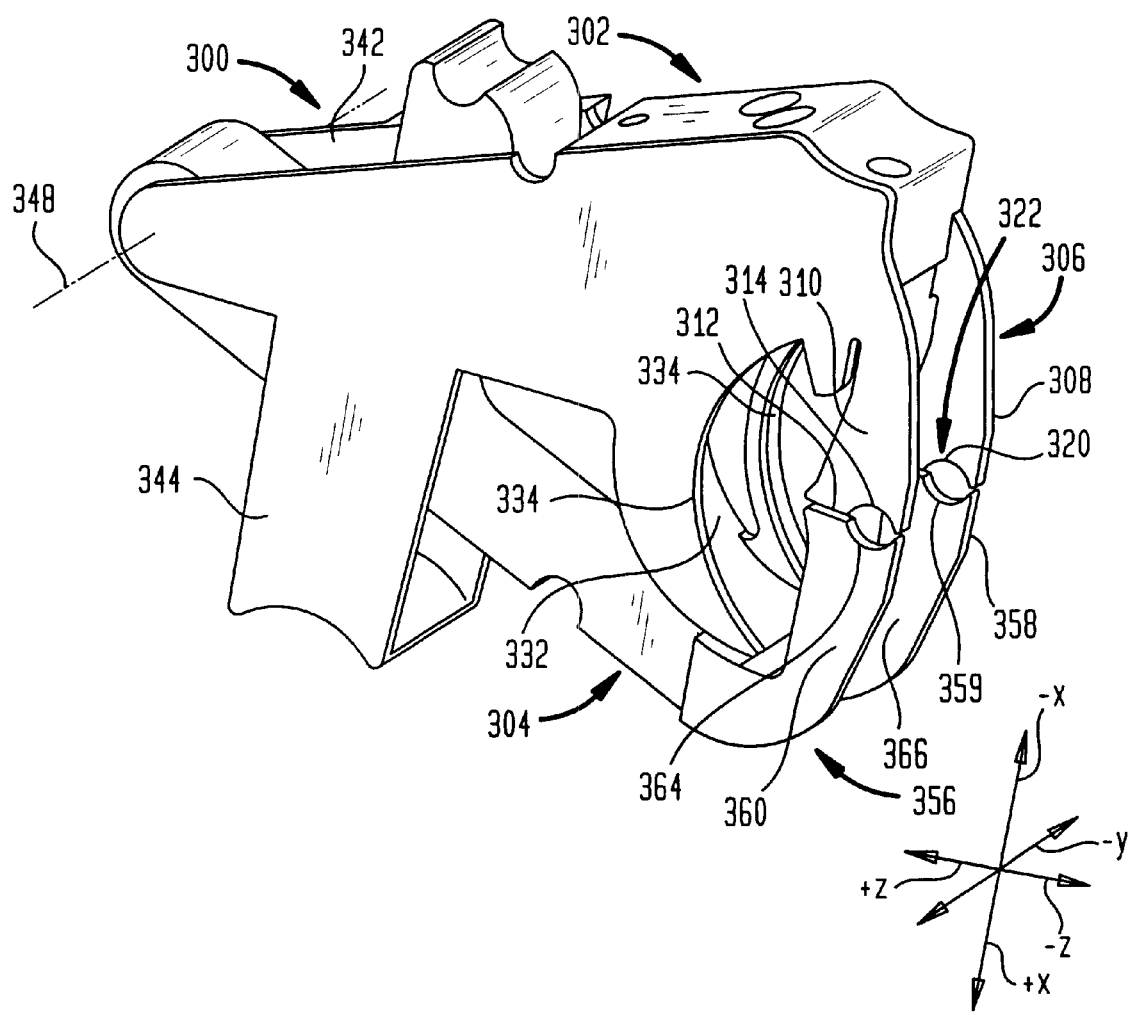
FIG. 8 is a perspective view depicting certain elements of apparatus according to a further embodiment of the invention.
Figure 9:
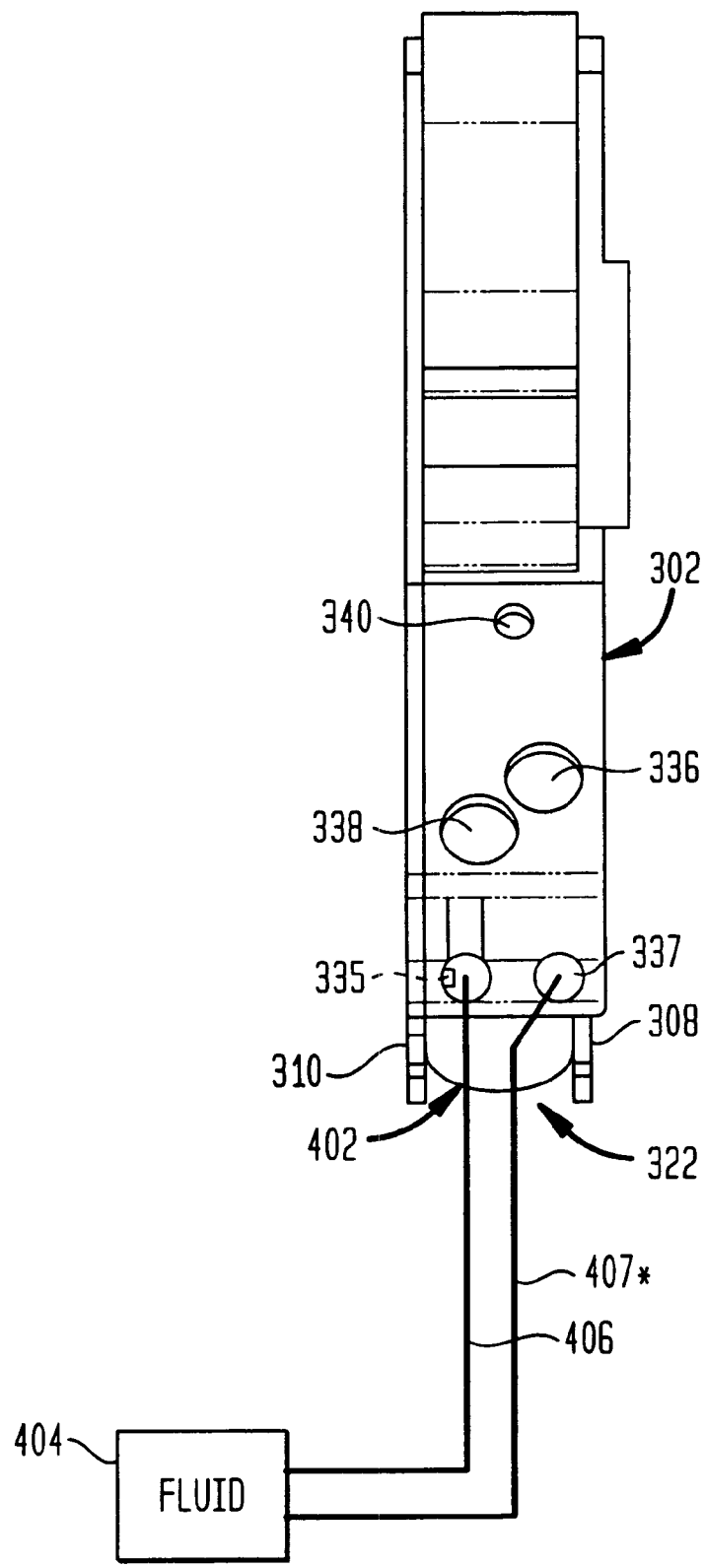
FIG. 9 is an elevational view of the elements shown in FIG. 8.
Figure 10:
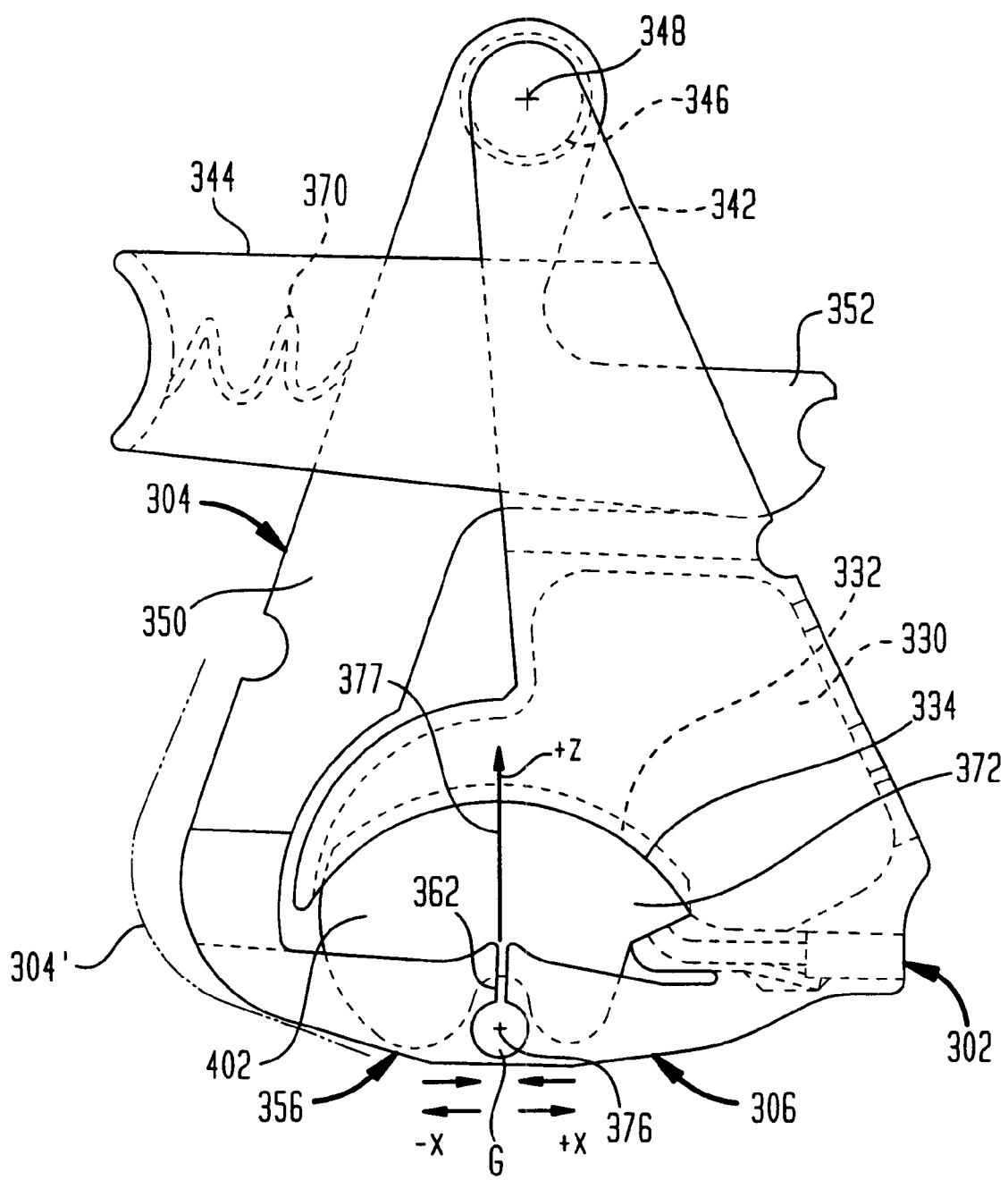
FIG. 10 is a further elevational view of the elements shown in FIGS. 8 and 9.
Figure 11:
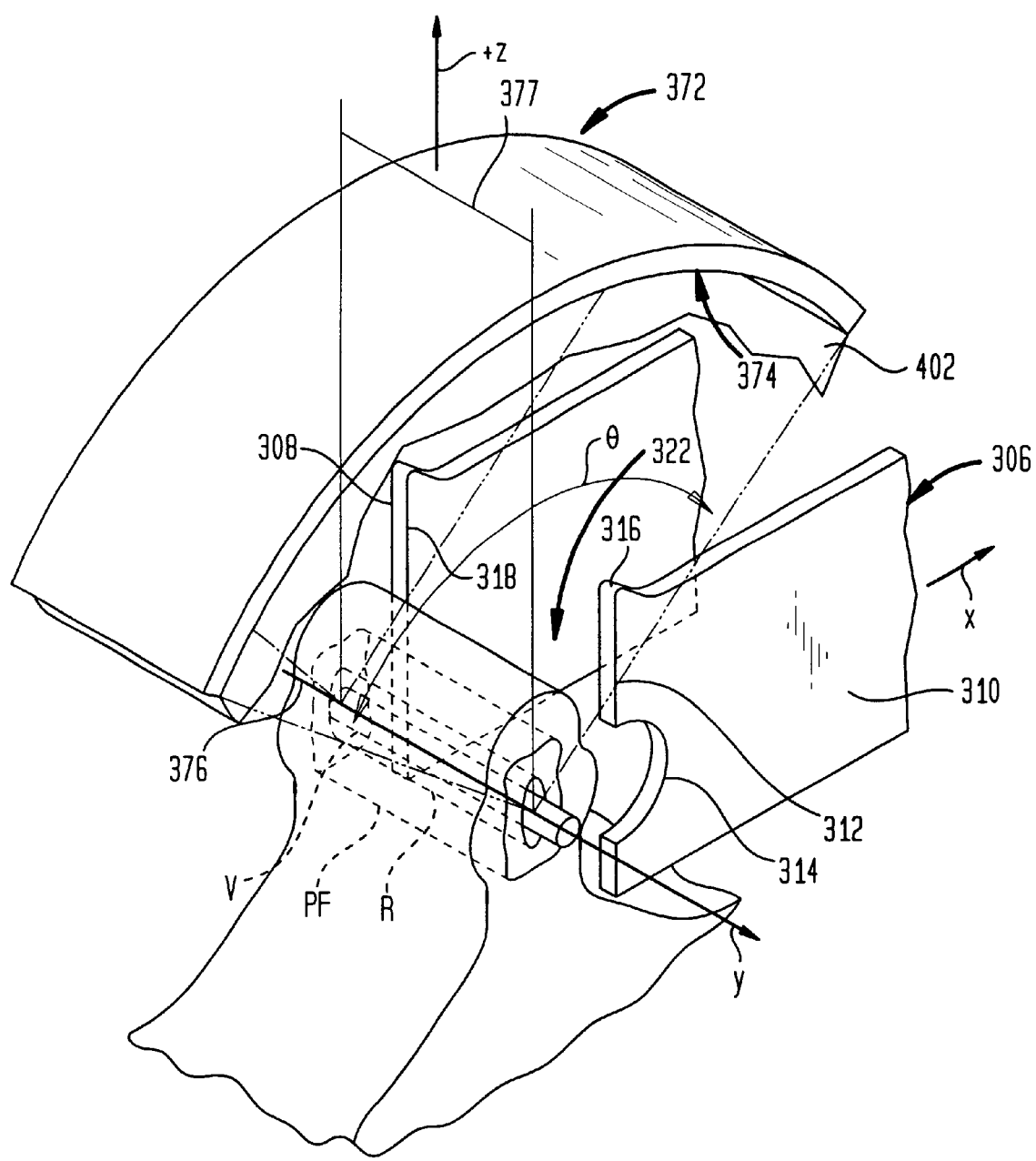
FIG. 11 is a diagrammatic perspective view depicting portions of the apparatus shown in FIGS. 8–10 in conjunction with a portion of a subject.
Figure 12:
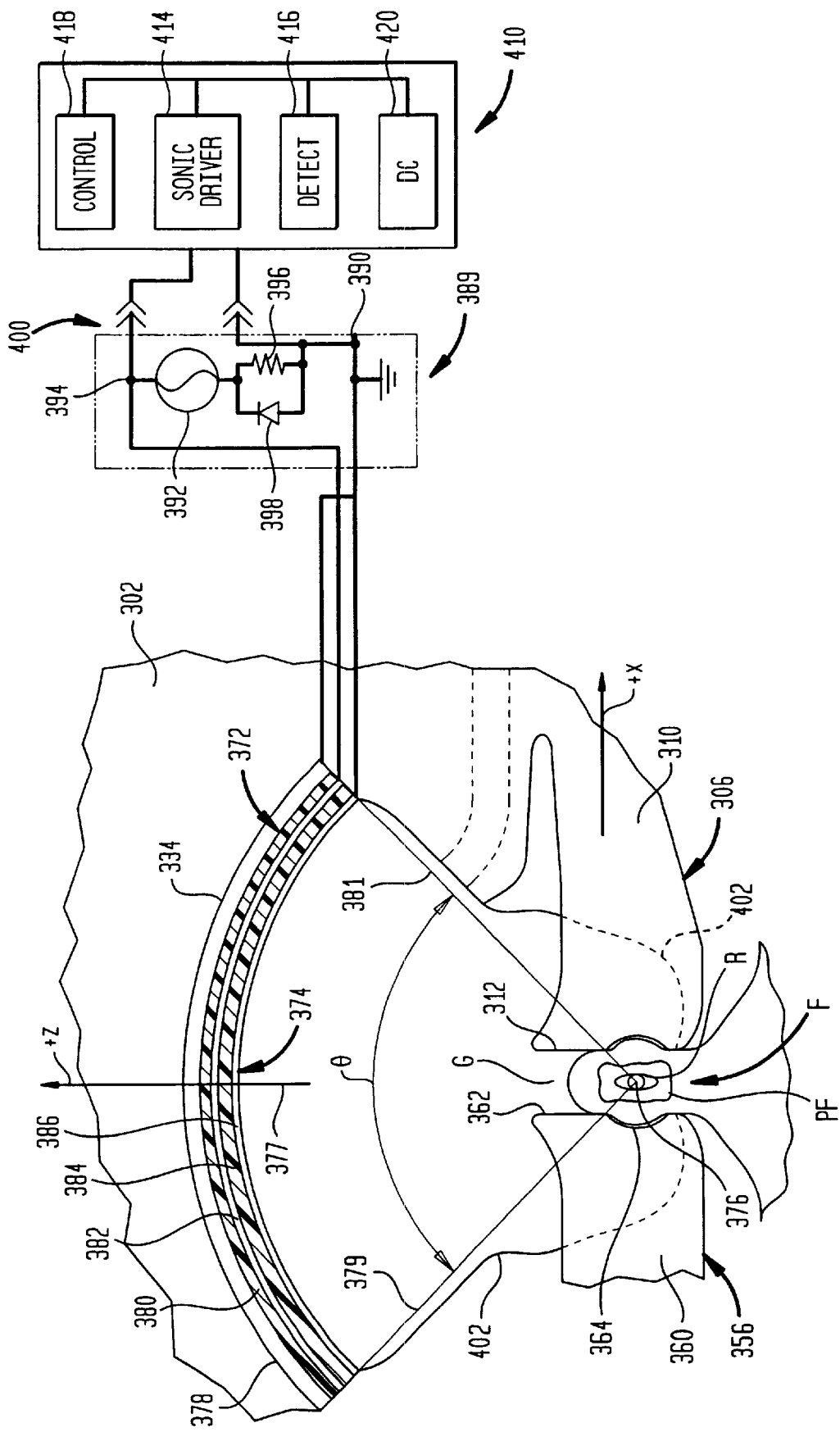
FIG. 12 is a diagrammatic, partially sectional view depicting additional portions of the apparatus of FIGS. 8–11 in conjunction with a portion of a subject.

Apparatus according a presently preferred configuration for performing vasectomies is depicted in FIGS. 8–12. This apparatus includes a housing 300 having a main portion 302 and an auxiliary portion 304. The main portion includes a first guide member 306 including a pair of elements 308 and 310. As best seen in FIG. 11, element 310 is a generally plate-like structure having an operative edge 312 with a recess 314 therein. The operative edge 312 extends generally in a first direction, denoted as a "Z" direction in FIGS. 8–12 for ease of reference. The Z direction towards the top of the drawing in FIGS. 10, 11 and 12 is referred to as the "+Z" or rearward direction, whereas the opposite direction is referred to as the forward or –Z direction. The recess 314 extends into the operative edge in a direction denoted as the "+X" direction in FIGS. 8, 10, 11 and 12, transverse to the Z directions. Merely by way of example, the operative edge 312 of the element may be about 10 mm long whereas recess 314 may be generally semicircular with a radius of about 2.5 mm.

Element 308 is substantially identical to element 310, and has a similar operative edge 318 with a recess 320 (FIG. 8) in the operative edge. The elements 308 and 310 forming the first guide member 306 are spaced apart from one another in a Y direction, transverse to the aforementioned X and Z directions, so that the elements 308 and 310 of the first guide member 306 define a first space 322 therebetween. For example, the distance between elements 308 and 310 in the Y direction may be about 12–13 mm. However, the operative edges and recesses of elements 308 and 310 are aligned with one another in the X and Z directions.

The main portion 302 of the housing includes wall structure defining a chamber 330 (FIG. 10), to the rear of guide member 306. The chamber has an opening 332 (FIG. 8) bounded by a pair of arcuate transducer support ledges 334 facing forwardly, toward the guide member. The main portion 302 of the housing also defines a pair of transducer fluid cooling ports 336 and 338 and a signal cable port 340 (FIG. 9) communicating with interior of chamber 330. The main portion 302 of the housing also defines a pair of sonic transmission fluid ports 335 and 337 (FIG. 9) and channels extending through the main portion to the vicinity of transducer mounting ledges 334.

The main portion 302 of the housing further defines an opening 342 (FIG. 8) extending through the housing in the X direction, rearwardly of chamber 330, and a hollow grip member 344 projecting from the remainder of the main portion in the −X direction in alignment with opening 342. The main portion of the housing also defines a pivot boss 346 (FIG. 10) having an axis 348 at the rearward end of the housing. Stated another way, axis 348 is offset in the +Z or rearward direction from the first guide member 306 and axis 348 extends generally in the Y direction.

The auxiliary portion 304 of the housing is mounted to the main portion for pivoting movement about axis 348. The auxiliary portion includes an arm 350 having a pivot bore (not shown) at its rearward end, the pivot boss 346 of the main portion being received in the pivot bore of arm 350. Arm 350 extends forwardly through the hollow grip member 344 of the main portion. Auxiliary portion 304 further includes a grip member 352 projecting transverse to the arm and extending in the +X direction, through opening 342 of the main portion so that an end of the grip member projects beyond the main portion 302.

The auxiliary portion 304 of the housing has a second guide member 356 at its forward end. The second guide member 356 includes a first element 358 (FIG. 8) and a second element 360. The first and second elements 358 and 360 of the second guide member 356 are flat, plate-like structures and are essentially mirror images of the first and second elements 308 and 310 of the first guide member 306. For example, the second element 360 of the second guide member defines an operative edge 362 extending generally in the Z direction and a recess 364 in the operative edge extending into the element in the −X direction. The first and second elements 358 and 360 are offset from one another in the Y direction and define a second space 366 (FIG. 8) between them. As best appreciated with reference to FIG. 8, the guide elements 358 and 360 of the second guide member 356 are aligned with one another in the X and Z directions. Also, the first element 358 defines a recess 359 in its operative edge. The first element 358 of the second guide member 356 is aligned, in the Y and Z directions, with the first element 308 of the first guide member 306. The second element 360 of the second guide member 356 is aligned in the Y and Z directions with the second element 310 of the first guide member 306. Thus, the recesses in the elements of the first and second guide members are aligned with one another. As also seen in FIG. 8, the elements of the first and second guide members 306 and 356 project in the −X and +X directions, respectively in front of the transducer mounting ledges 334.

A spring schematically depicted at 370 (FIG. 10) is connected between the main portion 302 and auxiliary portion 304 of the housing. The spring biases the auxiliary portion 304 in the counterclockwise direction about pivot axis 308 relative to the main portion 302 and thus biases the housing portions towards the closed position seen in FIG. 8–10. However, by engaging grips 352 and 344, and squeezing these grips towards one another, an operator can move auxiliary portion 304 relative to main portion 302 so that the auxiliary portion reaches the open position illustrated in broken lines at 304' in FIG. 10. As the housing portions move relative to one another towards the open position, the second guide member 356 moves generally in the −X direction, away from the first guide member 306. When the grip members are released, the auxiliary portion 304 moves back towards the closed position illustrated in solid lines and hence the second guide member 356 moves generally in the +X direction, toward the first guide member 306. In the closed position, the operative edges of the elements constituting the guide members confront one another and define a gap G having a central plane 377 (FIGS. 10 and 12) extending in the Y and Z directions between the confronting guide members. The spaces 322 and 366 defined by the guide members communicate with this gap.

The apparatus further includes an ultrasonic transducer 372. The transducer has an emitting surface 374 generally in form of a sector of a cylinder with its axis 376 extending in the Y direction. The emitting surface of the transducer encompasses an included angle θ (FIGS. 11 and 12) about axis 376. For use in apparatus intended to perform vasectomies, the radius of the emitting surface (the distance between the emitting surface and axis 376) may be, for example, about 20 mm, and the included angle θ may be, for example, about 2 radians (about 114°). The axial or Y-direction dimension of the transducer may be, for example, about 10–12 mm. The transducer preferably is a laminate structure and includes a substantially rigid backing plate 378 forming the rear side of the laminate. The backing plate may be formed from a conductive metal such as stainless steel about 0.004 inches (0.1 mm) thick, so that the backing plate also serves as a rear conductive layer. A first piezoelectric film 380, desirably formed from polyvinylidene fluoride or a polyvinylidene fluoride-trifluorethylene copolymer abuts the forward surface of backing plate 380. The thickness of this piezoelectric film is selected to provide a desired resonant frequency. For example, transducers intended to provide a resonant frequency of about 4 MHz may include a film 380 about 28 μm thick. Suitable piezoelectric polymer films are available, for example, from Measurement Specialties, Inc. of Norristown, Pa. A thin central conductive layer 382 overlies the forward surface of piezoelectric layer 380, whereas a second piezoelectric layer 384 identical to layer 380 overlies the forward surface of conductive layer 382. Conductive layer 382 may be formed by a coating of copper, silver or other metal deposited on one of the piezoelectric layers 380 or 384 using techniques common in the printed circuit industry. A front conductive layer 386, such as a stainless steel foil about 0.001 inches (0.25 mm) thick overlies the forward surface of the second piezoelectric layer 384.

The transducer may be formed by a process substantially as described in copending, commonly assigned U.S. patent application Ser. No. 09/532,614, filed on Mar. 22, 2000, the disclosure of which is hereby incorporated herein by reference. As described in greater detail in the '614 application, the various layers constituting the transducer may initially be provided as flat layers and laminated together between a pair of opposed mold pieces having the appropriate radii so as to deform the transducer to the desired radius. Thin coatings of epoxy or other suitable non-conductive laminating adhesive may be provided between the layers during the laminating procedure.

The transducer is attached to an auxiliary printed circuit 389 during or after the lamination process. Conductive layers 378 and 386 at the front and back surfaces of the transducer are connected to a local ground node 390 of the printed circuit, whereas the central conductive layer 382 is connected a hot or signal node 394. A resistor 396 and diode 398 are connected in parallel to one another and in series with a fuse 392 between the signal node 394 and the ground node 390. The printed circuit, or a cable connected to the printed circuit, is provided with an external connector 400 having separate contacts, one such contact being connected to the ground node 390 and another contact being connected to signal node 394.

Transducer 372 is mounted on the mounting ledges 334 of housing main portion 302 so that the transducer occludes opening 332, and so that the backing plate 378 (FIG. 12) is exposed to the interior of chamber 330. The printed circuit 389 may be physically mounted inside chamber 330 (FIG. 10) and may extend through the connection port 340 (FIG. 9) so that connector 400 is accessible for engagement with external circuitry. The transducer 372 and hence the axis 376 of the transducer is held in fixed position relative to the first guide member 306. The transducer is aligned, in the Y direction, with the spaces 322 and 366 (FIG. 8) defined by each of the guide members. The axis 376 of the transducer extends in the Y direction and is aligned in the Z direction with the recesses 314 and 320 in the elements of the first guide member 306, and with recesses 359 and 364 in the elements of the second guide member 356. Also, the axis is disposed adjacent the operative edges 312 and 318 (FIG. 11) of the first guide member, so that the axis 376 will be disposed in the gap G between the guide members. The transducer defines a central plane or medial plane including axis 376 and extending radially from the axis through the center of the arcuate transducer, bisecting the included angle θ of the transducer. The medial plane of the transducer is substantially coincident with the medial plane 377 of the gap between the guide members; the medial plane 377 extends in the Z and Y directions. The transducer also defines edge planes extending radially between axis 376 of the transducer and the circumferential edges of the transducer.

The apparatus further includes a flexible bag as, for example, a conventional latex or other distensible bag 402 overlying the forward or emitting surface 374 of transducer 372. As best seen in FIGS. 9, 10 and 12, bag 402, in an inflated condition, extends forwardly from the transducer and into the first space 322 defined between the elements 308 and 310 of the first guide member. Similarly, the bag, in its inflated condition, extends forwardly into the space 366 defined between the elements 358 and 360 of the second guide member 356.

The apparatus desirably also includes a source 404 of a substantially gas-free liquid which desirably has acoustic impedance close to that of the skin as, for example, a bag filled with degassed water. The fluid source is connected by flexible tubing 406 and 407 to the interior of bag 402 via the sonic fluid ports 335 and 337 (FIG. 9) so that fluid may be continually interchanged between the fluid source 404 and the interior of bag 402. All of the foregoing elements of the apparatus desirably are provided as a pre-assembled, disposable device.

In use, in a method according to one aspect of the invention, the aforementioned disposable device is associated with a reusable unit. Transducer coolant ports 336 and 338 are connected to a source of coolant fluid (not shown) in the reusable unit as, for example, by flexible tubing connected to these ports. The fluid source continually circulates a coolant fluid such as chilled water through these ports and through chamber 330, so that the coolant fluid cools transducer 372. The reusable unit desirably also includes a peristaltic pump (not shown) associated with tube 406 or other device for impelling degassed fluid into bag 402 from source 404. The reusable unit may also include a throttling clamp (not shown) on line 407 for restricting the flow from bag 402 back to fluid source 404 and thus maintaining a desired level of pressure within bag 402. The reusable unit may also include an appropriate chiller (not shown) for chilling the fluid in source 404 or for chilling the fluid as it circulates into or out of bag 402.

The electrical connector 400 of the printed circuit 389 is connected to a mating connector attached to a control and drive unit 310. The control and drive unit includes a conventional ultrasonic driver 414 for applying ultrasonic excitation signals at a frequency corresponding to the resonant frequency of transducer 374, desirably between about 1 and about 10 MHz, most desirably about 4 MHz. Unit 410 also includes a detector 416 adapted to detect electrical signals at the drive frequency appearing on the terminals 400 of the connector and measure the amplitude of such signals. The driver 414 and detector 416 are linked to a conventional electronic control computer 418 so that the control computer can command driver 418 to apply drive signals of a desired amplitude at desired times and so that the control computer can command detector 416 to measure electrical signals appearing on terminals 400 at desired times and report the amplitude of such signals. The reusable electronic unit 410 also includes a DC current source and resistance measurement unit 420. Unit 420 is arranged to apply a voltage having a selected polarity across terminals 400 and monitor the current flowing through the terminals. Unit 420 is linked to control computer 418 so that unit 420 can be actuated by the control computer 418 and will report current values to the computer.

The operator engages grips 352 and 344 and moves auxiliary portion 304 of the housing to the open position 304' (FIG. 10), thus moving the second guide member 356 away from the first guide member 306. The operator desirably applies an ultrasonic coupling gel to the bag 402, to the skin of the scrotum or both. Ultrasonic coupling gels are commonly used in ultrasonic imaging techniques; such gels have acoustic impedance close to that of the skin. The operator gathers a fold of skin of the patient's scrotum containing the vas deferens. The vas deferens normally can be detected by manual palpation of the skin. The operator places the fold F into the gap G between the operative edges of the first and second guide members and allows the guide members to move towards one another gently under the influence of spring 370 until the operative edges of the guide members engage the fold. In this process, the operator positions the fold so that the vas deferens V extends generally in the Y direction of the apparatus, and is lodged between the recesses 314, 322, 359 and 364 in the operative edges of the elements constituting the guide members. The fold F is thus pinched between the guide members, with the vas deferens extending generally in the Y direction and substantially coincident with the axis 376 of the transducer. In this condition, the fold F projects generally in the plus Z direction, towards transducer 372. Also, the mid plane of the fold is substantially aligned with the medial plane 377 of the transducer. The guide members grip the fold and maintain the housing, and hence transducer 372 substantially in a constant position relative to the fold of skin and the tissue within the skin, including the vas deferens V.

Fluid source 404, and the associated elements of the reusable unit are actuated to inflate bag 402 and to maintain a constant flow of cool, gas-free fluid through the bag. As indicated above, the bag bulges forwardly into spaces 322 and 366 defined by the guide members. As best appreciated with reference to FIG. 12, the bag 402 bulges forwardly (in the −Z direction) around fold F and substantially encompasses the fold, so that the bag extends forward along the fold on opposite sides of the transducer medial plane 377. Also, the bag lies forwardly or in the minus Z direction of the edge planes 379 and 381 defined by transducer 372.

Control computer 418 of the electronic unit 410 first commands DC unit 420 to apply a DC voltage across terminals 400 so that diode 398 is reverse biased and substantially blocks current flow. In this condition, the current flowing through the terminals will be almost entirely a function of the resistance of resistor 396. The reported current flow or resistance value is compared by the control computer to a set of predetermined acceptable values. The value of resistor 396 indicates one or more properties of the transducer 372 in the particular disposable unit. Preferably, the value of the resistor indicates the sonic conversion efficiency of the transducer, i.e., a relationship between electrical signal power applied to the transducer and sonic power output by the transducer. As described in greater detail in co-pending, commonly assigned U.S. patent application Ser. No. 09/596,678, filed Jun. 19, 2000, the disclosure of which is hereby incorporated by reference herein, the control computer can use this information to select the value of sonic drive signals to be applied to the transducer in later stages of the process. Thus, for a relatively efficient transducer, the control computer will command the sonic driver to apply lower-power drive signals and for a relatively inefficient transducer the control computer will command the sonic driver to apply higher-power drive signals, so that the sonic power produced by the transducer will have substantially the desired value despite variations between various transducers in different disposable units. After determining the resistance of resistor 396 in this manner, the control computer 418 commands the DC unit 420 to apply a voltage of the opposite polarity across terminals 400, so that diode 398 is forward-biased and sufficient current flows through fuse 392 to open or "blow" the fuse. This disables the diode and resistor.

The control computer then actuates the sonic driver 414 to apply a short, low-power initial monitoring pulse of ultrasonic-frequency signals. That pulse is applied to transducer 372 and converted by the transducer to a corresponding initial monitoring pulse of ultrasonic energy. The ultrasonic pulse propagates through the fluid within bag 402 and into the tissue constituting the fold F. Echoes from the tissue within the fold return through the fluid in the bag and impinge on the transducer. The signals impinging on the transducer are converted back to electrical signals which appear at terminals 400. Thus, the signals appearing at terminals 400 at a time $t_{eA}$ after termination of the initial monitoring pulse equal to the propagation time or time of flight for signals to travel to axis 376 and return, typically tens or hundreds of microseconds, will represent an ultrasonic echo from the tissue surrounding axis 372 and hence from the tissue surrounding the vas deferens. Echoes at a slightly shorter time $t_{eS}$ after termination of the initial monitoring pulse will represent ultrasonic echoes from the interface between bag 402 and the skin covering fold F.

The control computer actuates detector 416 to monitor electrical signals appearing after termination of the initial monitoring pulse. The amplitude of these electrical signals represents the amplitude of the echoes. If the indicated amplitude of such return signals, particularly at time $t_{eS}$ corresponding to signals returned from the skin interface, is above a pre-selected threshold, this indicates that an air bubble or other element having ultrasonic impedance different from that of the fluid in the bag and different from that of the tissue is present. Typically, this indicates an air bubble at the interface between the bag and the tissue. If the amplitude of the echoes is above this threshold, the control computer terminates operation and issues a warning signal to the operator. The warning signal can be displayed by any conventional device for producing a human-perceptible signal as, for example, a bell or other audible warning device, a warning light or an indication on a conventional computer screen.

Provided that the amplitude of the echoes is not above this first threshold, the control computer records amplitudes of the electrical signals at time $t_{eA}$ corresponding to echoes from the tissue surrounding the vas deferens or transducer axis as a reference value.

The control computer then deactivates the detector and actuates sonic driver 414 to apply a first heating or therapeutic pulse of ultrasonic energy. Here again, the electrical energy provided by the sonic driver is converted to ultrasonic energy by transducer 372 and propagates through the fluid within the bag and into the fold F. The ultrasonic energy is focused into a focal region R extending substantially along the Y axis. The focal region is formed by constructive interference between ultrasonic energy emitted by different regions of the transducer. The focal region is defined as a region in which the ultrasonic intensity differs from the maximum ultrasonic intensity by less than a predetermined amount. Preferably, the focal region is defined as the region in which the ultrasonic intensity is within about −6 dB of the peak intensity. As best appreciated with reference to FIG. 11, the focal region is generally in the form of a rectangular slab or plane lying generally in the Y-Z plane, along the medial plane of the transducer. That is, the thinnest dimension of the focal region is in the X directions. The Y dimension of the focal region is close to the Y dimension of the transducer itself. The Z dimension of the focal region typically is larger than the X dimension. For a transducer of about 20 mm radius and included angle θ of about 2 radians operating at 4 MHz, the Z dimension of the focal region is on the order of 1 mm, whereas the X dimension of the focal region is on the order of 0.3–0.4 mm. The focal region extends substantially along the mid plane 377 of the transducer and encompasses axis 376. Thus, the focal region encompasses the axis 376 of the transducer and hence intercepts the vas deferens. The applied sonic energy heats the tissue constituting the wall of the vas deferens and surrounding the interior opening of the vas deferens.

Because the fold projects generally in the Z direction and is generally in the form of a slab lying in the Y-Z plane, and because the medial or central plane of the fold is close to the mid plane 377 of the transducer. The focal region fits well within the interior of the fold. Stated another way, the boundary of the focal region is remote from the skin surface. Moreover, the ultrasonic energy is well focused within the focal region, so that the ultrasonic power intensity outside of the focal region but near the focal region is substantially lower than the power within the focal region. Stated another way, the power intensity desirably drops off sharply outside of the focal region. One measure of the quality of the focus is the size of a region referred to herein as a "perifocal" region PF, schematically shown in FIGS. 11 and 12, containing all locations having power intensity greater than or equal to a preselected value which is lower than the power intensity in the focal region. For example, this preselected value may be −10 dB below the peak power intensity. In this case, outside of the perifocal region, the power intensity is more than −10 dB lower than the peak intensity and hence −4 dB or more below the power intensity at the border of the focal region R. Where the power intensity drops off sharply outside of the focal region, the perifocal region is only slightly larger than the focal region. As seen in FIGS. 11 and 12, the perifocal region PF also fits within the fold of tissue, so that the boundary of the perifocal region lies inside the skin.

This placement of focal and perifocal regions is highly desirable to minimize absorption of ultrasonic energy at the skin. The skin is highly sensitive to heat; excessive heating of the skin can cause severe discomfort or even burning. The ability to heat the vas deferens or other target region to a temperature sufficient to kill the tissue without unacceptable heating of the skin is directly related to the ratio between ultrasonic power dissipation at the skin and ultrasonic power dissipation at the target. The ultrasonic power dissipation at any location the product of the ultrasonic power intensity and the ultrasonic absorptivity at such location. The skin, and the interface between the skin and the bag or other sonic transmission medium, typically has higher ultrasonic absorptivity than the internal structures. For example, the ultrasonic attenuation of the vas deferens is on the order of 1 dB/cm (measured at 1 MHz), whereas the comparable ultrasonic attenuation for human scrotal skin (taken from a cadaver) is on the order of 2.4 dB/cm. Canine scrotal skin has ultrasonic attenuation of about 5.5 dB/cm. Moreover, in the specific case of vas deferens or other spermatic ducts, the target region lies very close to the skin surface; typically, the vas deferens lies about 2 to about 6 mm from the interior surface of the skin, whereas the skin is about 1.5 mm thick. Therefore, it is particularly desirable to provide a small perifocal region in treatment of the vas deferens or other spermatic duct. Most desirably, the perifocal region extends about 2 mm or less in any direction from the center of the focal region, and desirably about 1.5 mm or less.

The size and shape of the focal and perifocal regions are related to the f-number of the transducer 372 and to the wavelength of the ultrasonic waves emitted by the transducer. The f-number is the focal length divided by the aperture size. For a transducer in the form of a cylindrical segment, the pertinent f-number is the radius of the transducer divided by the length of a chord of the segment. The chord length increases, and f-number decreases, with the included angle θ. Thus, a cylindrical-segment transducer having an included angle θ of about 2 radians has an f-number of about 0.5. f-numbers substantially below 1 are preferred, about 0.75 or less being more preferred and about 0.5 or less being most preferred where small focal and perifocal regions are desired. At frequencies of a few MHz and below, the size of the focal and perifocal regions varies directly with wavelength and inversely with frequency. Thus, to provide small focal and perifocal regions, ultrasonic frequencies of about 3–5 MHz, are preferred, 4 MHz being most preferred.

Figure 13:
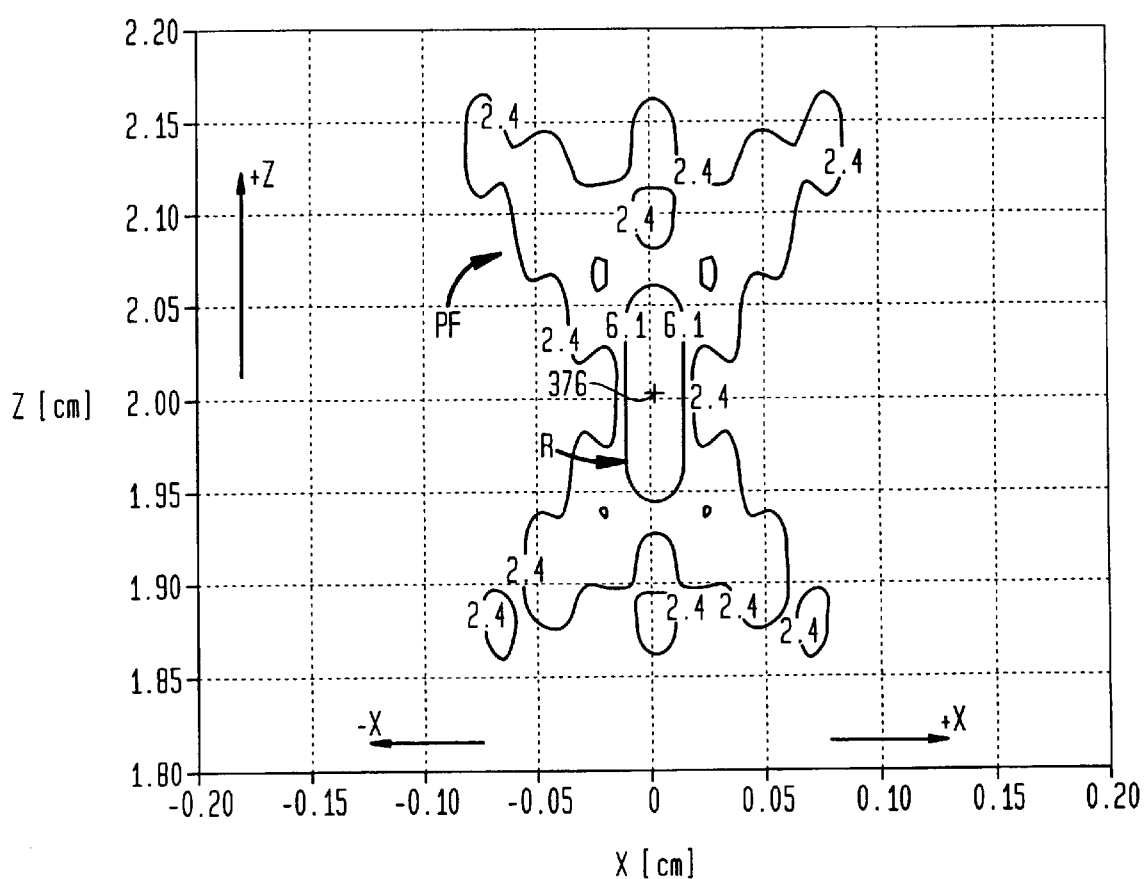
FIG. 13 is a graph depicting sonic focus regions in the embodiment of FIGS. 8–12.

FIG. 13 is a plot derived from a computer simulation of the focal and perifocal regions for a transducer having an included angle of 2 radians at operating at 4 MHz. The contour lines correspond to lines of constant intensity. The perifocal region PF has a maximum dimension, in the +Z or rearward direction, of about 1.5 mm from the center of the focal region. Moreover, the perifocal region has greater dimensions in the Z directions than in the X directions, and hence is well-matched to the shape and orientation of the fold. By contrast, an otherwise comparable transducer with an included angle of 1 radian and an f-number of 1 yields a perifocal region with a maximum extent, in the Z direction, of more than 1 cm from the center of the focal region. Such a transducer would place the skin within the perifocal region, making it more difficult to heat the vas deferens without also heating the skin.

Even with the preferred transducers, there is some heating of the skin. This effect is counteracted by the cooling effect of the fluid within bag 402.

After application of the first heating pulse, the control computer 418 actuates the sonic driver to apply a first in-process monitoring pulse in substantially the same way as discussed above with reference to the initial monitoring pulse. Here again, the monitoring pulse is reflected by the interface between the skin and bag 402 and by the tissue within the fold adjacent to axis 376. The resulting echoes again impinge on transducer 372 and are again converted to electrical signals which are detected by detector 416 in substantially the same way as discussed above. The control computer compares the value of these electrical signals for time $t_{eA}$ for the in-process monitoring pulse with the corresponding reference values recorded for the initial monitoring pulse at the corresponding echo times $t_{eA}$.

The difference between the value for the electrical signals resulting from an in-process monitoring pulse and the reference value represents a change in the echogenicity of the tissue at the focal region resulting from a change in temperature. This difference can be used as a measure of the heating effect in the focal region. In one control scheme, a set point is selected so that a difference equal to the set point indicates heating equal to the desired amount of heating. In this scheme, the computer terminates the operation when the difference equals the set point. Typically, after the first heating pulse, the difference is less than the set point and hence the computer commends driver 414 to repeat the cycle, so that another heating pulse is applied followed by a further in-process monitoring pulse. This cycle of operations is continued until the tissue surrounding axis 376 has been heated to the desired degree. Typically, application of a few watts of ultrasonic power for a total heating time or aggregate duration of all of the heating pulses equal to a few tens seconds is sufficient to heat the tissue to about 60–80° C. and thus kill the tissue of the vas deferens.

In a variant of this control scheme, the set point selected so that when the difference between the value of the electrical signals for $t_{eA}$ for an in-process monitoring pulse and the reference value is equal to the set point, the heating effect is slightly less than that required to produce the desired occlusion. The computer is arranged to command continued application of ultrasonic heating pulses for a preselected time or apply a preselected number of heating pulses after the difference reaches the set point, and then terminates the heating process. In more elaborate control schemes, several reference values are acquired for echo times corresponding to several locations within or near the focal region, using one or more initial monitoring pulses prior to application of a heating pulse, and differences are determined for each of these locations based on signals from subsequent in-process monitoring pulses in the same manner. A similar reference value can be acquired using one or more initial monitoring pulses for echo time $t_{eS}$, corresponding to the echoes from the skin. A difference between the value of electrical signals for time $t_{eS}$ resulting from an in-process monitoring pulse and the reference value for $t_{eS}$ represents a change in echogenicity at the skin. A difference more than a preselected maximum indicates that the skin has heated to an unacceptable degree. The control computer can be arranged to terminate the operation, issue a warning signal or both if this condition occurs. Alternatively, the computer may delay application of the next heating pulse or reduce the intensity of the next heating pulse.

Other forms of feedback control, such as magnetic resonance thermometry or even invasive temperature measurement can be employed to control the process. The temperature of the skin can be monitored as, for example, by thermocouples mounted on the apparatus such as on bag 402, provided that the thermocouples do not substantially interfere with propagation of the ultrasonic waves. Alternatively, the process can be operated in an open-loop manner, without any feedback control. The control computer can be programmed to actuate the sonic driver to deliver excitation signals as heating pulses, or a continuous stream of excitation signals for a preselected time or times. In this arrangement, the control computer can be replaced by a simple timer or by manual control of the driver.

Once the tissue has been heated to the desired degree and the control computer terminates operation of the sonic driver and detector, the computer issues a signal to the operator that the process is complete. The operator removes the disposable unit from the patient by squeezing grips 352 and 344 (FIG. 10) to force the auxiliary element 304 of the housing away from the main element 302 and thereby move the guide members 306 and 356 away from one another to release the fold F. The disposable unit is then discarded. Because fuse 392 was automatically opened or "blown" during use of the device as discussed above, the disposable unit cannot be reused. Any attempt to reuse the disposable unit will result in DC unit 420 reporting a nearly infinite resistance reading to the control computer at the start of the process.

Numerous variations and combinations of the features discussed above can be utilized. For example, the single-element polymeric transducer discussed above with reference to FIGS. 8–13 can be replaced by a multi-element transducer, or by a ceramic transducer or transducer array. Also, the physically curved transducer can be replaced by an equivalent flat transducer with a focusing lens or by a flat transducer array excited by signals phased to produce the desired focusing effect. Also, the transducer 214 of FIGS. 6–7, and the transducer 372 of FIGS. 8–11 can be replaced by a unit incorporating the outlet ends of waveguides, the inlet ends of such waveguides being connected to transducers located at other regions of the housing or even to transducers mounted separately from the housing as discussed above with reference to FIG. 5. Regardless of whether the transducers are physically mounted to the housing or connected to the housing through waveguides, they are operatively associated with the housing in the sense that the ultrasonic waves generated by the transducers are provided at the operative region of the housing.

Figure 14:
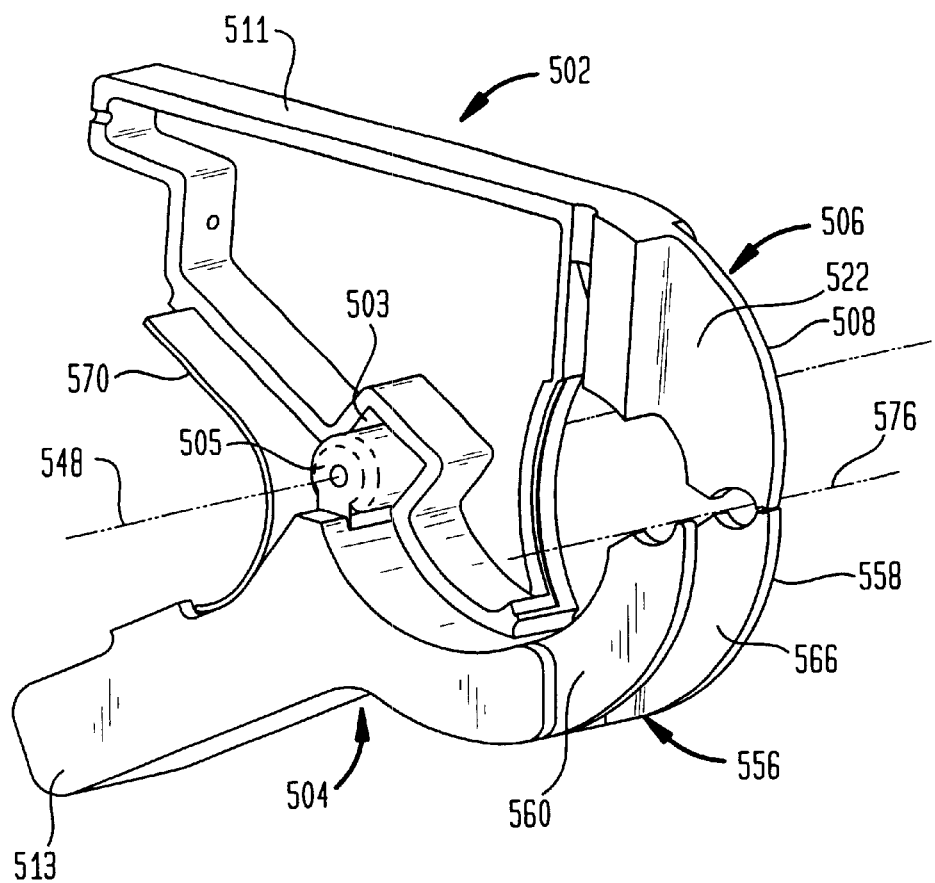
FIG. 14 is a diagrammatic, cutaway perspective view depicting elements of apparatus according to a further embodiment of the invention.

The particular mechanical constructions shown above can be varied. For example, as seen in FIG. 14, apparatus according to another embodiment of the invention includes a housing having a first portion 502 (seen in cutaway view in FIG. 14) and a second portion 504 mounted to one another by an interengaged boss 503 and slot 504 for pivoting movement about a pivot axis 548. Housing portion 504 has a guide member 556 at its forward end. Guide member 556 includes elements 558 and 560 spaced apart from one another in the direction parallel to axis 548, and defining a space 566. Housing portion 502 has a similar guide member 506 including two elements spaced apart from one another in the direction parallel to pivot axis 548 and defining a space 522 between them; only one of such elements 508 is visible in the cutaway view of FIG. 14. The guide members 556 and 508 are similar to the guide members 306 and 308 discussed above with reference to FIGS. 8–12. Housing element 502 includes a handle 511 projecting rearwardly of pivot axis 548, whereas housing portion 504 includes a similar handle 513. A spring 570 is disposed between the handle portions. The operator can manipulate the housing by the handles, and can force guide members 508 and 556 away from one another by squeezing the handles together. In other respects, the apparatus is substantially the same as the apparatus of FIGS. 8–12, and is used in the same way. Here again, a cylindrical-sector transducer (not shown) is mounted to the housing so that the axis 576 of the transducer extends in the gap G between the guide members. In this embodiment as well, the sonic transmission element extends into the space defined by each of the guide members so that the sonic transmission element envelops the fold of tissue engaged by the guide members.

The housing, and the mechanical arrangement used to move the guide members can be further varied, beyond the configurations illustrated. Any mechanical, electromechanical, hydraulic or pneumatic arrangement which can move the guide members with respect to one another to engage a portion of the subject's body without injuring the subject and without obstructing the ultrasonic waves can be employed. In yet another variant, only one guide member is provided and the pinched portion of the subject's body is manually held by the physician in engagement with the guide member.

Figure 15:
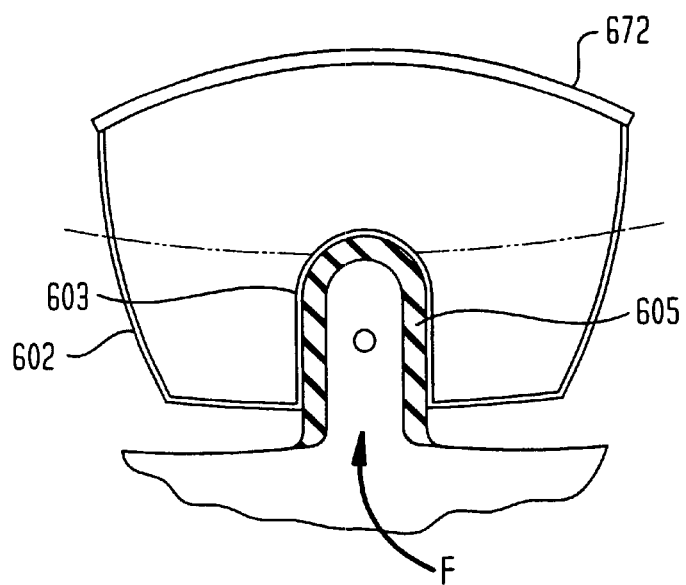
FIG. 15 is a fragmentary sectional view depicting portions of apparatus according to a further embodiment of the invention.

The flexible bag sonic transmission element, such as bag 402, can be replaced in whole or in part by a mass of gel or other deformable material having appropriate sonic transmission properties. The bag or other sonic transmission element can be provided with a pre-formed notch in its forwardly-facing surface to facilitate engagement of the bag with the fold of tissue. Also, to minimize any tendency of the bag to push the fold of tissue out of engagement with the guide members, the bag can be attached to the elements of the housing as, for example, to one or both of the guide members, so that the housing or guide members restrain the bag against movement in the forward or –Z direction. As seen in FIG. 15 a sonic transmission element may include as a hollow shell 602 formed from a polymer such as polyimide or other substantially non-distensible polymer, and may define a notch 603 in the forwardly-facing surface. The surface of the shell bounding the notch is thin enough so that it does not substantially impede sonic transmission. The remainder of the shell may be thicker, or may be fastened to one or both of the guide members or to some other portion of the housing, or both. The wall of the shell may be integral with one or both guide members. In this arrangement, the wall of the shell will not collapse into the notch and will not bear directly on the fold F of tissue received within the notch. The space inside the shell is filled with water or other liquid or gel medium having appropriate acoustic impedance. The sonic transmission medium in this embodiment includes a thick layer of gel 605 disposed within the notch and enveloping the fold F. The gel 605 and the medium within the shell cooperatively provide a continuous ultrasonic path through a sonic transmission medium extending from the transducer 672 to the fold F and enveloping the fold.

In a further variant (not shown), the region of the subject including the tissue to be treated, and at least a part of the apparatus including the transducer and guide members, may be immersed in a bath of a liquid or gel to provide the sonic transmission medium extending between the transducer and the subject. For example, in performing a vasectomy, the scrotum and apparatus may be immersed in water. The bath may be cooled and/or agitated to enhance heat transfer from the skin or other tissue surface. Such agitation may be continuous or intermittent, and desirably does not introduce air bubbles into the bath. The bath desirably extends into the spaces defined by the guide members, so that the bath provides a sonic transmission medium enveloping the fold.

In a further variant, the procedure can be performed at multiple points along the length of a tubular anatomical structure. For example, in the case of a vasectomy, a transducer as discussed above with reference to FIGS. 8–13 can be shifted along the axis of the vas deferens to treat two or more regions of the wall of the vas. These regions may be spaced apart from one another or may overlap one another. The housing may be arranged to allow movement of the transducer relative to the guide members in a direction parallel to the axis of the anatomical structure. In the case of a cylindrical sector transducer such as that of FIGS. 8–13, the housing may be arranged to allow movement of the transducer relative to the guide members in a direction parallel to the axis of the transducer, i.e., in the Y direction as seen in FIGS. 8–12.

The features discussed above with reference to performing vasectomies and can be applied to treatment of other spermatic ducts as, for example, to the epididymus. The same features can be applied to other tubal occlusion procedures, as, for example, occlusion of blood vessels lying near the skin surface, whereas the features discussed with reference to tubal occlusion procedures in general also can be applied to performance of vasectomies. Moreover, the features discussed above can be applied to treatment of bodily structures other than tubular structures lying near the skin surface. Merely by way of example, a lesion lying near the skin surface can be ablated by the same techniques as are used to perform a vasectomy. Also, these features can be applied to treatment of other anatomical structures through body surfaces other than the skin as, for example, through the lining of the gastrointestinal tract, respiratory tract, genitourinary tract or other space which is naturally open to the exterior environment. In this case, the instrument is inserted into such space but remains outside of the body itself, and hence the procedure is substantially non-invasive. Further, the apparatus can be employed in invasive procedures as well, as where the instrument is inserted into a surgically-created opening in the body. For example, a lesion or structure within an internal organ can be treated by surgically exposing the organ and heating the lesion through the tissue forming the exterior surface of the organ. The techniques described will above minimize damage to the organ surface in much the same way as they minimize heating of the skin.

To enhance heating of the tissue constituting a tubular anatomical structure, an ultrasonic contrast medium can be injected into the tubular anatomical structure. The contrast medium may be selected so that speed of sound in the contract medium is different from the speed sound in anatomical tissues and, desirably, lower than the speed of sound in such tissues. Desirably, the acoustic impedance of the contrast medium, or of a portion of the contrast medium, differs from the acoustic impedance of the surrounding tissues. The acoustic impedance of a medium is the product of the density and the speed of sound in the medium. A large difference in acoustic impedance between media at an interface forms a substantially reflective interface, so that sonic waves including ultrasonic waves, impinging on the interface are reflected. This promotes absorption at the boundary between the medium and the surrounding tissue. Where such a reflective contrast medium is present in the bore of a tubular anatomical structure, this promotes absorption at the interface between the medium and the tissue constituting the wall of the structure. For example, air or other gas can be employed as a reflective ultrasonic contrast medium. The contrast medium alternatively may be a liquid or a solid such as a solid probe or wire. Most preferably, the contrast medium is a dispersive medium, i.e., a medium which causes dispersion of ultrasonic waves. The preferred dispersive media include particles dispersed in a matrix or surrounding substance, most typically a fluid such as a liquid. The particles have acoustic impedance different from the acoustic impedance of the surrounding matrix. For example, the particles may be gas-filled micro spheres such as hollow micro spheres of a protein or other biocompatible material. Micro particles of this type, specifically gas-filled micro spheres surrounded by a shell of human serum albumin, are commercially available under the trademark ALBUNEX from the Molecular Biosystems company of San Diego, Calif. Such micro particles may be introduced in into the body suspension in a suitable biologically compatible liquid as, for example, saline solution or other aqueous liquid. Alternatively, such micro particles may be dispersed in the body fluids naturally occurring within the subject. In a further alternative, a dispersive contrast medium can be formed by introducing bubbles of air or other gas into a naturally-occurring body fluid or by introducing a dispersion of bubbles in a liquid, i.e., a foam, into the body from an external source. A dispersive contrast medium has a higher ultrasonic absorptivity than the surrounding tissue, so that the ultrasonic energy directed onto the region of the body containing the contrast medium is absorbed preferentially by the medium, so that the medium is heated more rapidly than the surrounding tissue. Heat transfer from the medium to the tissue assists in heating of the tissue.

Increased absorption provided by a contrast medium facilitates heating of the tissues and also can enhance selectivity of the heating process because tissue in the immediate vicinity of the medium will be heated to a greater degree than tissue remote from the medium. For example, where a contrast medium is provided within a tubular anatomical structure, the wall of structure will be heated selectively even if the ultrasonic energy impinging of the structure has the same intensity as ultrasonic energy impinging on other tissue surrounding the structure. The enhanced selectivity can be used, for example, in applying hyperthermia to tissues which lie near to delicate structures or sensitive organs such as nerves.

The contrast medium is exogenous. That is, at least a part of the contrast medium is introduced into the body from outside of the body. The contrast medium can be withdrawn from the body immediately after completion of the heating step. However, if the contrast medium is biologically compatible, it may remain in place and be absorbed into the body. The contrast medium also may be used in hyperthermia procedures which do not involve a tubular anatomical structure. For example, a bolus of a contrast medium may be injected into a solid tumor or other solid tissue to be ablated, to enhance ablation of tissue around the bolus. In a further variant, the contrast medium may include a drug or other biologically active substance, and hyperthermia may be used to potentiate the action of the drug.

The contrast medium also enhances ultrasonic imaging procedures. The contrast medium also may provide enhanced contrast in other imaging modalities. For example, air or other gases typically provide low MRI response, and hence media which include gas-filled particles or bubbles can provide low MRI response. Depending on the properties of the surrounding tissues, this may provide enhanced contrast. Other materials, such as liquids incorporating gadolinium, can provide a bright, clearly-distinguishable line in an MRI image. The contrast medium may alter (and typically lowers) the cavitation threshold, i.e., the amount of sonic energy with can be absorbed before cavitation or formation of gas bubbles within the subject occurs. In typical hyperthermia procedures, this is considered disadvantageous. However, in tubal occlusion procedures according to this aspect of the invention, mechanical damage due to cavitation can help to promote formation of scar tissue occluding the tubular structure. In other instances, where the contrast medium raises the cavitation threshold, the sonic energy application procedure can be extended to provide greater heating and promote scarring. Cavitation can be sensed to provide feedback control of the process, as by detecting the sounds created by cavitation. The process control can be set to terminate the energy application upon the occurrence of cavitation; or a preselected time thereafter; or once a preselected amount of energy has been applied after the onset of cavitation. Other, more conventional forms of feedback control can be used, such as magnetic resonance thermometry.

As these and other variations and combinations of the features discussed above can be used, the foregoing description of the preferred embodiments should be taken by way of illustration, rather than by way of limitation, of the present invention.

What is claimed is:

1. A method of sterilizing a mammalian subject comprising the step of directing energy from outside of the subject's body, through the skin of the scrotum into the body and onto the tissue constituting a spermatic duct to thereby kill at least some of such tissue at a location along the length of the spermatic duct, whereby scar tissue will form and occlude the spermatic duct.

2. A method as claimed in claim 1 wherein said step of directing energy includes directing ultrasonic energy.

3. A method as claimed in claim 2 wherein said directing step includes pinching the scrotum of the subject and capturing the spermatic duct in the pinched region, and applying energy through the skin covering the pinched region.

4. A method as claimed in claim 3 wherein said step of applying energy on the exterior of the pinched region includes the step of applying a probe adapted to emit energy to the pinched region of the scrotum.

5. A method as claimed in claim 4 further comprising the step of maintaining said probe in a preselected position relative to the pinched region by means of one or more guide members connected to said probe and engaged with said pinched region.

6. A method as claimed in claim 5 wherein said one or more guide members include a pair-of opposed guide members projecting from said probe and wherein said pinched region of the scrotum is engaged between said pair of opposed guide members.

7. A method as claimed in claim 6 wherein said pinched region of the scrotum projects generally in a Z direction relative to said guide members and said probe, and said pinched region and said spermatic duct extend generally in a Y direction transverse to said Z direction, and wherein said step of directing ultrasonic energy includes emitting the sonic energy from one or more transducers defining an emitting surface offset from the pinched region in said Z direction, the method further comprising the step of providing a sonic transmission element extending between the emitting surface and the skin of said engaged region.

8. A method as claimed in claim 7 wherein said emitting surface is substantially in the form of a sector of a cylindrical surface having an axis extending in said Y direction, the axis of the emitting surface being disposed within the pinched region of the scrotum.

9. A method as claimed in claim 8 wherein said transducer has an f-number of about 0.5 or less.

10. A method as claimed in claim 7 wherein a first one of said one or more guide members includes first and second elements spaced apart from one another in said Y direction and defining a first space therebetween, and wherein said sonic transmission element extends into said first space and engages the skin of the pinched region in said first space.

11. A method as claimed in claim 10 wherein a second one of said one or more guide members includes first and second elements spaced apart from one another in said Y direction and defining a second space therebetween, and wherein said sonic transmission element extends into said second space and engages the skin of the pinched region in said second space.

12. A method as claimed in claim 2 wherein said spermatic duct is the vas deferens.

13. A method as claimed in claim 1 wherein said step of directing energy is performed so as to deliver a predetermined dose of energy to the tissue surrounding the spermatic duct, without feedback control of such dose during the directing step.

14. A method as claimed in claim 1 further comprising the steps of monitoring one or more effects of the applied energy and controlling the dose of energy delivered to the tissue based upon said monitoring to thereby provide feedback control of the applied dose.

15. A method as claimed in claim 14 wherein said one or more effects include echogenicity of tissue surrounding the spermatic duct.

16. A method as claimed in claim 14 wherein said step of applying energy includes the step of actuating one or more transducers to apply heating pulses of ultrasonic energy and said monitoring step includes the step of monitoring signals generated by at least one of said one or more transducers responsive to ultrasonic energy impinging thereon.

17. A method as claimed in claim 16 further comprising the step of actuating at least one of said one or more transducers to emit one or more monitoring pulses of ultrasonic energy interspersed with said heating pulses, said monitoring step including the step of detecting signals generated by at least one of said one or more transducers responsive to echoes of said monitoring pulses impinging thereon.

18. A method as claimed in claim 17 wherein said one or more monitoring pulses includes an initial monitoring pulse prior to application of said heating pulses and one or more in-process monitoring pulses after application of at least one heating pulse, and wherein said monitoring step includes comparing signals produced by at least one of said transducers responsive to said in-process monitoring pulses with signals produced by the same one of said transducers responsive to the initial monitoring pulse.

19. A method as claimed in claim 1 further comprising the step of reversing the occlusion of said spermatic duct by surgically removing said scar tissue and reconnecting regions of said spermatic duct on opposite sides of said scar tissue.

20. A method of occluding a tubular anatomical structure in the body of a mammalian subject comprising the step of directing ultrasonic energy from outside of the subject's body, into the body and onto the tissue constituting the tubular anatomical structure to thereby kill at least some of such tissue at a location along the length of the anatomical structure, whereby scar tissue will form and occlude the anatomical structure.

21. A method as claimed in claim 20 wherein said directing step includes maintaining a probe having one or more ultrasonic transducers associated therewith and adapted to emit ultrasonic energy so that said ultrasonic energy will be focused in a focal region at known disposition relative to the probe at a preselected disposition relative to a portion of the subject's body incorporating the anatomical structure so that the focal region encompasses the anatomical structure.

22. A method as claimed in claim 21 wherein said step of maintaining said probe in a preselected disposition relative to the portion of the subject's body is performed by engaging one or more guide members connected to said probe and with such portion of the subject's body.

23. A method as claimed in claim 22 wherein said one or more guide members include a pair of opposed guide members and wherein said portion of the subject's body is pinched between said pair of opposed guide members.

24. A method as claimed in claim 23 wherein said portion of the body generally in a Z direction relative to said guide members and said probe, and said pinched portion and said anatomical structure extend generally in a Y direction transverse to said Z direction, and wherein said step of directing ultrasonic energy includes emitting the sonic energy from one or more transducers defining an emitting surface offset from the pinched region in said Z direction, the method further comprising the step of providing a sonic transmission element extending between the emitting surface and the skin of said pinched portion.

25. A method as claimed in claim 24 wherein said emitting surface is substantially in the form of a sector of a cylindrical surface having an axis extending in said Y direction, the axis of the emitting surface being disposed within the pinched portion of the subject's body.

26. A method as claimed in claim 24 wherein a first one of said one or more guide members includes first and second elements spaced apart from one another in said Y direction and defining a first space therebetween, and wherein said sonic transmission element extends into said first space and engages the skin of the pinched region in said first space.

27. A method as claimed in claim 26 wherein a second one of said one or more guide members includes first and second elements spaced apart from one another in said Y direction and defining a second space therebetween, and wherein said sonic transmission element extends into said second space and engages the skin of the pinched portion in said second space.

28. A method as claimed in claim 20 wherein said step of directing energy is performed so as to deliver a predetermined dose of energy to the tissue surrounding the anatomical structure, without feedback control of such dose during the directing step.

29. A method as claimed in claim 20 further comprising the steps of monitoring one or more effects of the applied energy and controlling the dose of energy delivered to the tissue based upon said monitoring to thereby provide feedback control of the applied dose.

30. A method as claimed in claim 29 wherein said one or more effects include echogenicity of tissue surrounding the anatomical structure.

31. A method as claimed in claim 29 wherein said step of applying energy includes the step of actuating one or more transducers to apply heating pulses of ultrasonic energy and said monitoring step includes the step of monitoring signals generated by at least one of said one or more transducers responsive to ultrasonic energy impinging thereon.

32. A method as claimed in claim 31 further comprising the step of actuating at least one of said one or more transducers to emit one or more monitoring pulses of ultrasonic energy interspersed with said heating pulses, said monitoring step including the step of detecting signals generated by at least one of said one or more transducers responsive to echoes of said monitoring pulses impinging thereon.

33. A method as claimed in claim 32 wherein said one or more monitoring pulses includes an initial monitoring pulse prior to application of said heating pulses and one or more in-process monitoring pulses after application of at least one heating pulse, and wherein said monitoring step includes comparing signals produced by at least one of said transducers responsive to said in-process monitoring pulses with signals produced by the same one of said transducers responsive to the initial monitoring pulse.

34. A method as claimed in claim 20 further comprising the step of reversing the occlusion of said tubular structure surgically by removing said scar tissue and reconnecting regions of said tubular structure on opposite sides of said scar tissue.

35. Apparatus for occluding a tubular anatomical structure including:
  (a) a probe including a housing having an operative region and one or more ultrasonic transducers operatively associated with said housing, said transducers being adapted to deliver ultrasonic energy at a focal region having a known disposition relative to said operative region of said housing; and
  (b) one or more guide members projecting from said housing for engaging a portion of a subject's body to hold that portion of the body in position relative to the operative region of the housing so that the focal region will lie at a known disposition to the body portion engaged by the guide members.

36. Apparatus as claimed in claim 35 wherein said one or more guide members are adapted to engage the skin of the subject's body covering the engaged portion of the body.

37. Apparatus as claimed in claim 35 wherein said one or more guide members include first and second opposed guide members adapted to receive a pinched portion of the body and maintain said operative region in preselected disposition relative to said pinched region.

38. Apparatus as claimed in claim 37 wherein one or both of said guide members is movable relative to the housing so that said guide members can be moved toward and away from one another so as to pinch a portion of the subject's body in a gap between said guide members.

39. Apparatus as claimed in claim 38 wherein guide members are adapted to pinch said portion of the body therebetween so that the pinched portion projects generally in a Z direction relative to said guide members and said probe, said one or more transducers defining an emitting surface offset in said Z direction from the gap between said guide members.

40. Apparatus as claimed in claim 39 wherein said emitting surface is substantially in the form of a sector of a cylindrical surface having an axis extending in a Y direction transverse to said Z direction, said guide members being movable towards and away from one another generally in an X direction transverse to said Y and Z directions, the axis of the emitting surface being disposed within the gap between said guide members.

41. Apparatus as claimed in claim 39 wherein said transducer has an f-number less than 1.

42. Apparatus as claimed in claim 39 wherein said first guide member includes first and second elements spaced apart from one another in said Y direction and defining a first space therebetween.

43. Apparatus as claimed in claim 42 wherein a second one of said one or more guide members includes first and second elements spaced apart from one another in said Y direction and defining a second space therebetween.

44. Apparatus as claimed in claim 43 further comprising a sonic transmission element extending between the emitting surface and the gap between the guide members so that the flexible sonic transmission element will engage the skin of the pinched portion of the body held in said gap, said sonic transmission element extending into said spaces defined by said guide members.

45. Apparatus as claimed in claim 38 wherein said one or more transducers are adapted to deliver ultrasonic energy at a focal location, the apparatus further including means for moving said focal location relative to said housing as said guide members move towards and away from one another.

46. Apparatus as claimed in claim 38 wherein said one or more transducers include one or more transducers mounted to a carriage, said carriage being movable in carriage movement directions so that said carriage moves toward said guide members as said guide members move toward one another.

* * * * *

UNITED STATES PATENT AND TRADEMARK OFFICE
CERTIFICATE OF CORRECTION

PATENT NO. : 6,599,256 B1
DATED : July 29, 2003
INVENTOR(S) : David E. Acker et al.

It is certified that error appears in the above-identified patent and that said Letters Patent is hereby corrected as shown below:

Title page,
Insert Item -- Related U.S. Application Data
[63] THIS APPLN CLAIMS BENEFIT OF 60/153,432 09/10/1999. --.

Column 7,
Lines 28-36, delete the paragraph break following the words "remains intact," so that the paragraph reads -- The procedure affords several significant advantages over conventional surgical vasectomy. It is non-invasive. Moreover, the vas deferens remains intact. To reverse the procedure, the vas deferens can be surgically isolated from the surrounding tissue. The region affected by the ultrasonic ablation can be dissected out and the resulting ends can be reunited with one another. Because the vas deferens is not cut in the original procedure, the problem of losing the ends does not arise. --.

Column 23,
Line 30, "body generally" should read -- body extends generally --.

Column 24,
Line 19, "pulses includes" should read -- pulses include --.
Line 59, "wherein guide" should read -- wherein said guide --.

Signed and Sealed this

Twenty-eighth Day of February, 2006

JON W. DUDAS
*Director of the United States Patent and Trademark Office*